(12) United States Patent
Blevins et al.

(10) Patent No.: US 8,093,306 B2
(45) Date of Patent: Jan. 10, 2012

(54) INTEGRATED BIOREFINERY FOR PRODUCTION OF LIQUID FUELS

(75) Inventors: Randy Blevins, West Des Moines, IA (US); Joshua B. Pearson, Englewood, CO (US); Harold A. Wright, Longmont, CO (US)

(73) Assignee: Rentech, Inc., Los Angeles, CA (US)

( * ) Notice: Subject to any disclaimer, the term of this patent is extended or adjusted under 35 U.S.C. 154(b) by 0 days.

(21) Appl. No.: 12/976,739

(22) Filed: Dec. 22, 2010

(65) Prior Publication Data
US 2011/0178185 A1 Jul. 21, 2011

(51) Int. Cl.
*C07C 27/00* (2006.01)
(52) U.S. Cl. ......... 518/705; 518/700; 518/702; 518/704
(58) Field of Classification Search .............. 518/700, 518/702, 704, 705
See application file for complete search history.

(56) References Cited

U.S. PATENT DOCUMENTS

| | | | |
|---|---|---|---|
| 4,585,798 A | 4/1986 | Beuther | |
| 4,609,679 A | 9/1986 | Wood et al. | |
| 5,036,032 A | 7/1991 | Iglesia | |
| 5,504,118 A | 4/1996 | Benham et al. | |
| 5,508,118 A | 4/1996 | Hayashi et al. | |
| 5,733,839 A | 3/1998 | Espinoza | |
| 6,075,062 A | 6/2000 | Zennaro et al. | |
| 6,136,868 A | 10/2000 | Culross et al. | |
| 6,262,131 B1 | 7/2001 | Arcuri | |
| 6,353,035 B2 | 3/2002 | Manzer | |
| 6,368,997 B2 | 4/2002 | Herron | |
| 6,451,864 B1 | 9/2002 | Wang | |
| 6,476,085 B2 | 11/2002 | Manzer | |
| 6,490,880 B1 | 12/2002 | Walsh | |
| 6,537,945 B2 | 3/2003 | Singleton et al. | |
| 6,558,634 B1 | 5/2003 | Wang et al. | |
| 6,648,662 B2 | 11/2003 | Shinzou et al. | |
| 7,084,180 B2 | 8/2006 | Wang et al. | |
| 7,375,142 B2 | 5/2008 | Pearson | |
| 7,732,171 B2 | 6/2010 | Blacker et al. | |
| 2003/0105171 A1 | 6/2003 | Subramanian et al. | |
| 2008/0098654 A1* | 5/2008 | Cherry et al. ............ | 48/101 |
| 2009/0062108 A1 | 3/2009 | Demirel et al. | |
| 2009/0075814 A1 | 3/2009 | Duvenhage et al. | |
| 2009/0298678 A1 | 12/2009 | Demirel et al. | |
| 2010/0181539 A1 | 7/2010 | Apanel | |
| 2010/0311570 A1 | 12/2010 | Duvenhage et al. | |

FOREIGN PATENT DOCUMENTS

WO WO 2009/113006 A2 * 9/2009

* cited by examiner

*Primary Examiner* — Jafar Parsa
(74) *Attorney, Agent, or Firm* — Porter Hedges LLP; Timothy S. Westby

(57) ABSTRACT

A method and system for reforming a carbonaceous feedstock comprising the steps, reforming the feedstock produce a first synthesis gas, subjecting a portion of the first synthesis gas to catalytic conversion, separating from the synthesis gas conversion product at least one byproduct, and utilizing at least a portion of the at least one byproduct during reforming of additional carbonaceous material. In certain instances, the method and system may be used to produce a liquid fuel.

18 Claims, 5 Drawing Sheets

INTEGRATED BIOREFINERY FOR PRODUCTION OF LIQUID FUELS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. Field of the Invention

This disclosure relates generally to a biorefinery and method for the conversion of carbonaceous feedstock into synthesis gas conversion products. More specifically, this disclosure relates to a biorefinery and method for the conversion of carbonaceous feedstock to liquid hydrocarbons via Fischer-Tropsch. Still more specifically, this disclosure relates to a biorefinery and method for the conversion of carbonaceous material to Fischer-Tropsch products wherein at least one byproduct of Fischer-Tropsch conversion is utilized to produce additional synthesis gas for Fischer-Tropsch synthesis.

2. Background of the Invention

Processes for the production of synthesis gas from carbonaceous materials utilize gasification of a feedstock comprising the carbonaceous materials in a so-called 'reformer' to produce a stream comprising synthesis gas (i.e. hydrogen and carbon monoxide; also known as 'syngas'). The product synthesis gas generally also comprises amounts of carbon dioxide and methane and may also comprise minor amounts of other components. Generation of synthesis gas is disclosed in numerous patents.

Synthesis gas produced via gasification of carbonaceous materials can be converted into other compounds in a so-called Fischer-Tropsch reaction. Fischer-Tropsch (FT) synthesis can be used to catalytically produce synthetic liquid fuels, alcohols or other oxidized compounds. FT synthesis occurs by the metal catalysis of an exothermic reaction of synthesis gas. Fischer-Tropsch (FT) technology can thus be utilized to convert synthesis gas to valuable products. Hydrocarbon liquid products of various Fischer-Tropsch processes are generally refined to produce a range of synthetic fuels, lubricants and waxes. Often, the Fischer-Tropsch process is performed in a slurry bubble column reactor (SBCR). The technology of converting synthesis gas originating from natural gas into valuable primarily liquid hydrocarbon products is referred to as Gas To Liquids (GTL) technology. When coal is the raw material for the syngas, the technology is commonly referred to as Coal-To-Liquids (CTL). Fischer-Tropsch technology is one of several conversion techniques included in the broader GTL/CTL technology. Desirably, the synthesis gas for subsequent production of valuable products via Fischer-Tropsch is produced from 'green' materials. For example, an environmentally-friendly system for the production of synthesis gas, which may subsequently be utilized to produce Fischer-Tropsch products, would desirably allow for the production of synthesis gas from carbonaceous materials, such as biomass, which may generally be considered waste materials.

The catalyst used in the Fischer-Tropsch reactor and, to some extent, the temperatures and pressures used will determine what products can be obtained. Some Fischer-Tropsch processes are directed to the production of liquid hydrocarbons. Such processes generally utilize iron-, ruthenium, or cobalt-based catalysts. Iron-based catalysts are generally operated with a synthesis gas having a molar ratio of hydrogen to carbon monoxide in the range of from about 0.7 to about 2.0. Cobalt-based catalysts are generally operated with a synthesis gas having a mole ratio of hydrogen to carbon monoxide in the range of from about 1.8 to about 2.2. For example, carbon monoxide and hydrogen can be converted to alkanes over a cobalt-thoria catalyst. U.S. Pat. No. 4,609,679 teaches the use of ruthenium combined with tantalum, niobium, vanadium or mixtures thereof to selectively catalyze for the production of methane. As mentioned hereinabove, other Fischer-Tropsch processes are directed toward the production of alcohols.

Accordingly, there is a need in the art for systems and methods for the production of synthesis gas conversion products from carbonaceous materials. Such systems and methods should preferably enable the environmentally-friendly production of synthesis gas conversion product, for example, by allowing the production of synthesis gas from sustainable and renewable feedstocks such as biomass, facilitating sequestration of carbon dioxide and/or reducing the amount of waste material produced.

SUMMARY

Herein disclosed are a system and method of producing synthesis gas conversion product. Disclosed herein is a method comprising reforming a carbonaceous feedstock to produce a first synthesis gas, subjecting at least a portion of the first synthesis gas to catalytic conversion into synthesis gas conversion product, separating from the synthesis gas conversion product at least one byproduct selected from the group consisting of (a) a tailgas comprising at least one component selected from carbon monoxide, hydrogen, methane and carbon dioxide; and (b) a spent catalyst product comprising synthesis gas conversion product and catalyst that has been at least partially deactivated, attrited, or both during catalytic conversion, and utilizing at least a portion of the at least one byproduct during reforming of additional carbonaceous material.

In further embodiments, the catalytic conversion comprises Fischer-Tropsch conversion of synthesis gas and the synthesis gas conversion product comprises liquid hydrocarbons. In embodiments, the catalyst is selected from the group consisting of iron-based Fischer-Tropsch catalysts. Further, the byproduct may comprise Fischer-Tropsch tailgas.

In embodiments, utilizing at least a portion of the byproduct during reforming of additional carbonaceous material comprises combusting at least a portion of the Fischer-Tropsch tailgas to provide heat for reforming additional carbonaceous material. The method may further comprise removing carbon dioxide from the Fischer-Tropsch tailgas.

In embodiments of the method, the byproduct comprises spent catalyst product comprising liquid hydrocarbons and catalyst. In embodiments, utilizing at least a portion of the byproduct during reforming of additional carbonaceous material comprises reforming at least a portion of the spent catalyst product with additional carbonaceous material.

In embodiments, the method further comprises preparing the carbonaceous feedstock by combining at least one carbonaceous material with superheated steam. Additionally, in embodiments, the carbonaceous feedstock is prepared at a pressure of between about 5 psig (34.5 kPa) to 45 psig (310.3 kPa).

In embodiments, the method further comprises providing a desired molar ratio of hydrogen to carbon monoxide in the first synthesis gas by controlling at least one parameter selected from the group consisting of the weight ratio of the at least one carbonaceous material to the superheated steam, the moisture content of the at least one carbonaceous material, the reforming temperature, and the reforming pressure. In embodiments, the reforming temperature is in the range of from about 1700° F. (926° C.) to about 2200° F. (1204° C.). In embodiments, the catalytic conversion comprises Fischer-Tropsch conversion of synthesis gas, wherein the synthesis gas conversion product comprises liquid hydrocarbons and wherein the desired molar ratio is in the range of from about 0.5:1 to about 2:1. In embodiments, the desired molar ratio is about 1:1.

In embodiments, the method comprises reducing the amount of at least one component selected from the group consisting of hydrogen, carbon monoxide, ash, tar, aromatics and carbon dioxide in the first synthesis gas.

In embodiments the catalytic conversion comprises conversion of synthesis gas into at least one component selected from the group consisting of alcohols and the catalyst favors the production thereof.

According to an embodiment of this disclosure the carbonaceous feedstock comprises biomass.

In embodiments, the method further comprises producing superheated steam utilizing the heat of a flue gas produced during reforming, the heat of the first synthesis gas, or both.

Also disclosed herein is a method of producing liquid hydrocarbons, comprising: reforming a carbonaceous feedstock that is solid, liquid, or both to produce a first synthesis gas comprising hydrogen and carbon monoxide, subjecting at least a portion of the first synthesis gas to Fischer-Tropsch conversion whereby at least a portion of the hydrogen and carbon monoxide in the first synthesis gas is catalytically converted into product comprising liquid hydrocarbons, separating from the product a Fischer-Tropsch tailgas comprising at least one component selected from carbon monoxide, hydrogen, methane and carbon dioxide, and combusting at least a portion of the Fischer-Tropsch tailgas to provide at least a portion of the heat for the reforming of additional carbonaceous feedstock.

The method may further comprise forming additional carbonaceous feedstock by combining, with superheated steam, at least one carbonaceous material and a spent catalyst stream comprising Fischer-Tropsch liquid hydrocarbons and catalyst that has been at least partially deactivated, attrited, or both during Fischer-Tropsch conversion.

Also disclosed herein is a method of producing liquid hydrocarbons, the method comprising: reforming a carbonaceous feedstock to produce a first synthesis gas comprising hydrogen and carbon monoxide; subjecting at least a portion of the first synthesis gas to Fischer-Tropsch conversion whereby at least a portion of the hydrogen and carbon monoxide in the first synthesis gas is catalytically converted into product comprising liquid hydrocarbons; removing from the Fischer-Tropsch conversion reactor a catalyst wax mixture comprising Fischer-Tropsch liquid hydrocarbons and catalyst removed from the reactor; and combining at least a portion of the catalyst wax mixture with at least one carbonaceous material and superheated steam; and reforming the combined material to produce additional synthesis gas.

The method may further comprise combusting at least a portion of a Fischer-Tropsch tailgas produced during Fischer-Tropsch conversion and comprising at least one component selected from the group consisting of carbon monoxide, hydrogen, carbon dioxide and methane to provide heat for reforming of additional carbonaceous feedstock.

Also disclosed herein is a system for the production of conversion products from synthesis gas, the system comprising: a mixing apparatus configured for mixing steam with at least one carbonaceous material to produce a reformer feedstock; a reformer configured to produce, from the reformer feedstock, a reformer product comprising synthesis gas comprising hydrogen and carbon monoxide; a synthesis gas conversion apparatus configured to catalytically convert at least a portion of the synthesis gas in the reformer product into synthesis gas conversion product and to separate from the synthesis gas conversion product a tailgas comprising at least one gas selected from the group consisting of carbon monoxide, carbon dioxide, hydrogen and methane; and one or more recycle lines fluidly connecting the synthesis gas conversion apparatus with the mixing apparatus, the reformer, or both.

In embodiments, the system comprises a recycle line fluidly connecting the synthesis gas conversion apparatus with at least one burner of the reformer, whereby at least a portion of the tailgas can be combusted to provide heat.

In further embodiments, the at least one carbonaceous material comprises biomass.

In embodiments, the mixing apparatus is a pressure vessel operable at a pressure of about 5 psig (34.5 kPa) to 45 psig (310.3 kPa). In further embodiments, the mixing apparatus comprises one or more cylindrical vessels having a conical bottom section, an inlet for superheated steam within the conical bottom section and an inlet for the at least one carbonaceous material at or near the top of the cylindrical vessel.

In embodiments the metallurgy of the reformer allows operation at a reformer temperature greater than or equal to about 1700° F. (926° C.) and a reformer pressure greater than or equal to about 5 psig (34.5 kPa). In embodiments, the reformer comprises: a cylindrical vessel containing a plurality of vertically-oriented coiled tubes fluidly connected with the mixing apparatus such that reformer feedstock may be introduced thereto; at least one burner configured to combust fuel to provide heat for the reforming and produce a flue gas; at least one outlet for reformer product; and at least one outlet for the flue gas.

In embodiments, each of the plurality of vertically-oriented coiled tubes has a vertical height in the range of from about 40 feet (12.2 m) to about 100 feet (30.5 m) and a coil length at least 4 times the vertical height. In further embodiments, the coil length is in the range of from about 4 to about 12 times the vertical height. In still further embodiments according to the disclosure, the metallurgy of the coiled tubes allows operation at a reformer pressure greater than or equal to about 45 psig (310.3 kPa).

In embodiments, the at least one burner is positioned substantially at, near, or below the bottom of the cylindrical vessel. In embodiments, outlets of each of the coiled tubes are manifolded into an outlet for the reformer product, wherein the manifold is positioned at, near, or below the bottom of the cylindrical vessel. In further embodiments according to the disclosure, the at least one outlet for flue gas is positioned at the top of the cylindrical vessel. In embodiments, the system further comprises a steam superheater configured to produce superheated steam utilizing heat transfer from the reformer flue gas.

In embodiments, the system further comprises feed preparation apparatus configured to comminute the at least one carbonaceous material, to dry the at least one carbonaceous material, or both. In embodiments, the feed preparation apparatus comprises at least one grinder and at least one separator configured to provide a carbonaceous material having an average particle diameter of less than about $3/16^{th}$ of an inch (0.47 cm).

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a more detailed description of embodiments of the present invention, reference will now be made to the accompanying drawings, wherein.

NOTATION AND NOMENCLATURE

Certain terms are used throughout the following description and claim to refer to particular system components. This document does not intend to distinguish between components that differ in name but not function.

As used herein, the term 'carbonaceous feedstock' includes not only organic matter that is part of the stable carbon cycle, but also fossilized organic matter such as coal, petroleum, and natural gas, and products, derivatives and byproducts thereof, such as plastics, petroleum coke and the like.

As used herein, the terms 'hot', 'warm', 'cool' and 'cold' are utilized to refer to the relative condition of various streams. That is, a 'hot' stream is at a higher temperature than a 'warm' stream, a 'warm' stream is likewise at a higher temperature than a 'cool' stream and a 'cool' stream is likewise at a higher temperature than a 'cold' stream. Such a stream may not 'normally be considered as such. That is a 'cool' stream may have a temperature that is actually high enough to be considered hot or warm in conventional, non-relative usage.

As used herein the term 'dry' as applied to a carbonaceous feed material is used to indicate that the feed material has a moisture content suitable for reforming, e.g. less than about 20 weight percent, and not to imply the complete absence of moisture.

DETAILED DESCRIPTION

I. Overview. Herein disclosed are a biorefinery and a method for producing synthesis gas conversion products such as, but not limited to, Fischer-Tropsch hydrocarbons. The disclosed biorefinery and method enable the use of renewable and sustainable carbonaceous materials, such as biomass, for the production of synthesis gas, the sequestration of carbon dioxide in multiple ways and locations, a reduction in the amount of waste for disposal (e.g. Fischer-Tropsch wax associated with spent catalyst), and a reduction in the amount of 'waste' tailgas. Accordingly, the disclosed biorefinery and process for producing synthesis gas conversion products therewith represent clean technologies. Such a biorefinery is significantly more environmentally-friendly than conventional biorefineries that produce synthesis gas for subsequent conversion from other sources, such as from natural gas.

Figure 1:
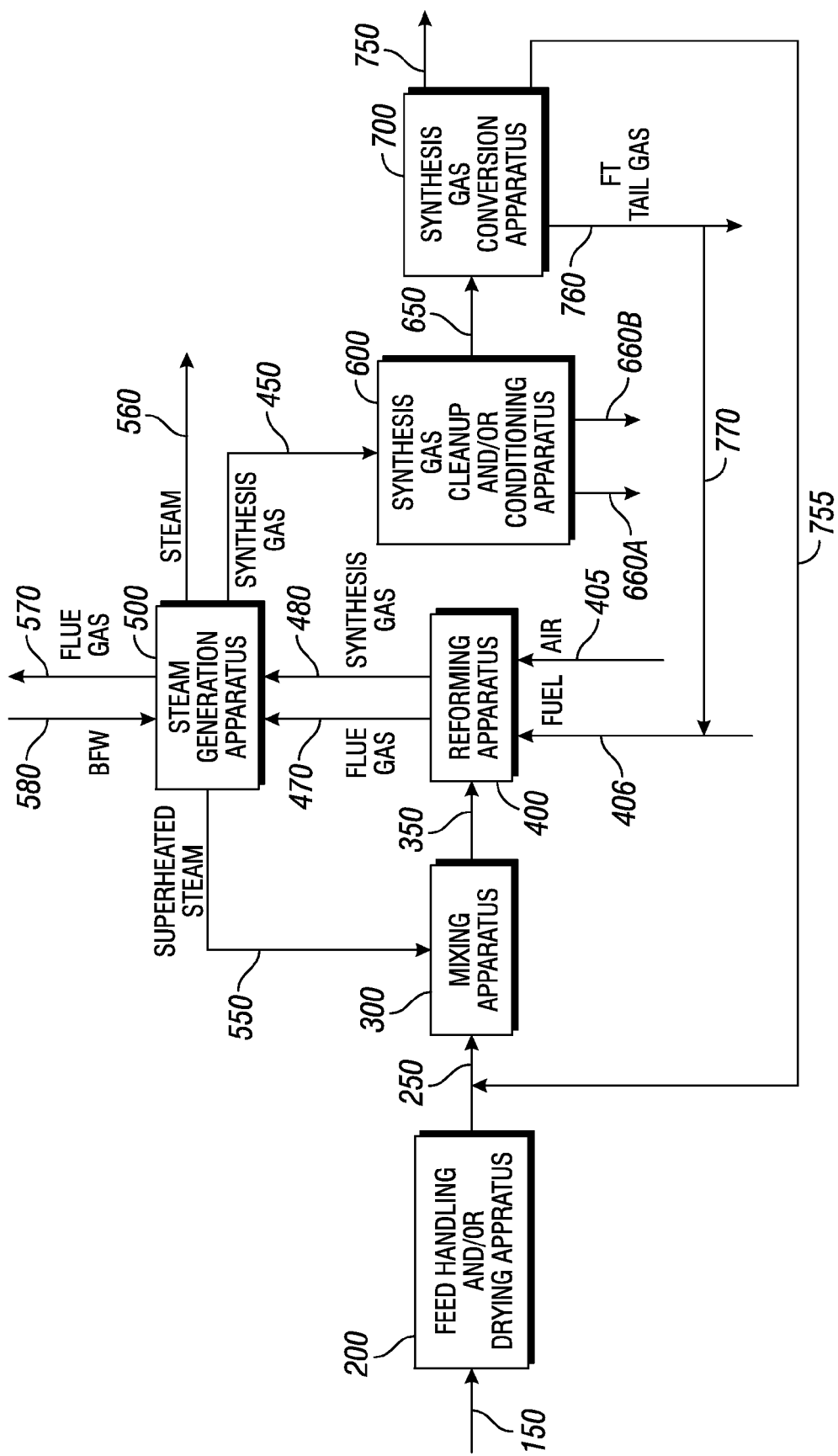
FIG. 1 is a schematic of a biorefinery suitable for carrying out the production of synthesis gas conversion products according to an embodiment of this disclosure.

II. Biorefinery. FIG. 1 is a schematic of a biorefinery 100 according to this disclosure. Biorefinery 100 comprises mixing apparatus 300, reforming apparatus 400, steam generation apparatus 500 and synthesis gas conversion apparatus 700. As discussed further hereinbelow, biorefinery 100 can further comprise feed handling and/or drying apparatus 200 and synthesis gas cleanup and/or conditioning apparatus 600. Each of the basic apparatus will be described in more detail hereinbelow.

Reforming Apparatus 400. Biorefinery 100 comprises reforming apparatus 400 (also at times referred to herein as 'reformer 400'). Description of reforming apparatus 400 will now be made with reference to FIG. 2, which is a schematic of a portion 100A of a biorefinery comprising mixing apparatus 300A, reformer 400A and steam generation apparatus 500A, according to an embodiment of this disclosure, and FIG. 3, which is a schematic of a portion 100B of a biorefinery comprising mixing apparatus 300B, reformer 400B and steam generation apparatus 500B, according to another embodiment of this disclosure.

Reformer 400A is a high temperature, high efficiency reformer. In embodiments, reformer 400 is a biomass reformer. Reformer 400A comprises a plurality of coiled tubes 410A, 410B surrounded by enclosure, cylindrical vessel or firebox 407. In embodiments, biomass reformer 400A is a cylindrical vessel. In embodiments, the cylindrical vessel 407 has a height H1 in the range of from about 40 feet (12.2 m) to about 100 feet (30.5 m), from about 50 feet (15.2 m) to about 100 feet (30.5 m), or from about 60 feet (18.3 m) to about 100 feet (30.5 m). In embodiments, coiled tubes 410 have an inside diameter (ID) of at least or about 2 inches (5.1 cm), at least or about 3 inches (7.6 cm), or at least or about 4 inches (10.2 cm). Coiled tubes 410 may be configured as cylindrical helices and may be oriented vertically within cylindrical vessel 407. In embodiments, each of the coiled tubes 410 has a total length or coil length that is at least 4, 5, 10, 15, 20 or 25 times the vertical height of the coiled tubes. In embodiments, each of the coiled tubes 410 has a total length in the range of from about 200 feet (61 m) to about 900 feet (274 m), from about 300 feet (91.4 m) to about 700 feet (213.4 m), or from about 350 feet (106.7 m) to about 650 feet (198.1 m).

In embodiments, the metallurgy of the coiled tubes is upgraded such that the tubes are operable at the high temperatures of operation of a high temperature reformer. A 'high' temperature reformer is operable at a temperature of at least 1093° C. (2000° F.). In embodiments, the coiled tubes are operable at temperatures up to 926° C. (1700° F.), 982° C. (1800° F.), 1038° C. (1900° F.), 1093° C. (2000° F.), 1149° C. (2100° F.) and a pressure of at least 2 psig (13.8 kPa), 5 psig (34.5 kPa), at least 20 psig (137.9 kPa), greater than or about 40 psig (275.8 kPa) or about 45 psig (310.3 kPa) or about 50 psig (344.7 kPa). In embodiments, the coiled tubes are fabricated from stainless steel or other high alloy steel, such as 310 stainless steel. In embodiments, the coiled tubes are fabricated from austenitic nickel-chromium-based superalloys or other high temperature alloys that are resistant to hydrogen attack and suitable for production of coiled helices, such as INCONEL™. In embodiments, the coiled tubes are fabricated from INCONEL™ 800 HT. In embodiments, the coiled tubes are designed to provide at least 100,000 hours of operation.

Figure 3:
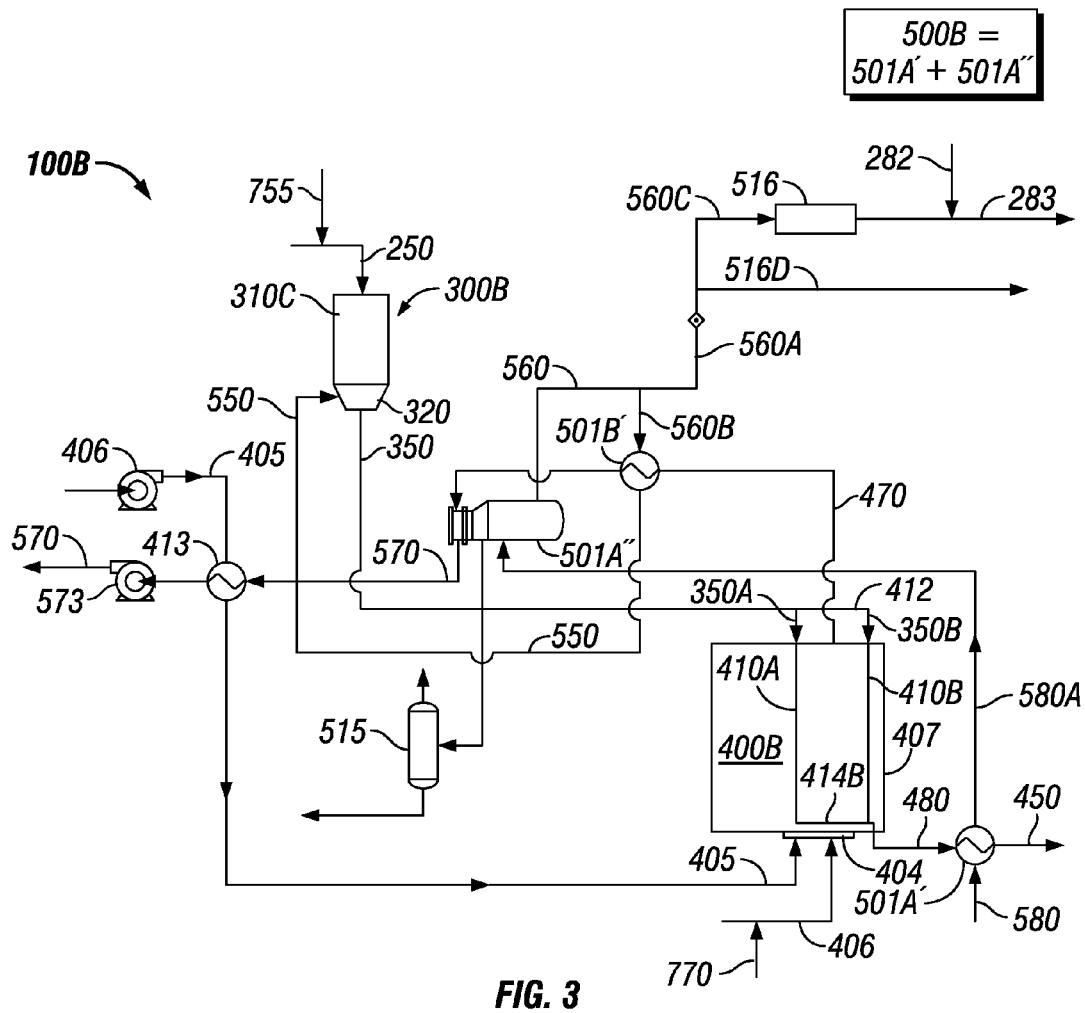
FIG. 3 is a schematic of suitable mixing apparatus, biomass reformer, and steam generation apparatus for use in the biorefinery of FIG. 1 according to another embodiment of this disclosure.

As shown in FIG. 3, a distributor or flow divider 412 can be positioned external or internal to firebox 407 for distributing a reformer feedstock comprising a mixture of cooled steam and dry carbonaceous material to the plurality of coiled tubes 410. In embodiments, distributor 412 is positioned external to vessel 407. In embodiments, distributor 412 is configured to provide substantially equal amounts of the reformer feed mixture to each of the coiled tubes 410.

Distributor 412 distributes reformer feed mixture to each of the plurality of coiled tubes 410 (410A and 410B indicated in the embodiment of FIG. 3) via one or more reformer feed inlet lines 350 (350A and 350B depicted in the embodiment of FIG. 3). In embodiments, mixing apparatus 300 (300A in FIG. 2; 300B in FIG. 3), further discussed hereinbelow, comprises a plurality of feed mixers 310 (mixers 310A and 310B depicted in FIG. 2; mixer 310C depicted in FIG. 3), the output of each of which is fed via one or more reformer feed inlet lines 350 (350A and 350B indicated in the embodiment of FIG. 2) into the coiled tubes 410.

The amount of superheated steam in the reformer feed mixture is a function of the nature of the carbonaceous material (i.e. the feedstock) used. In addition to steam necessary for carbonaceous feed transport, steam provides the additional hydrogen necessary to produce, from the feedstock, suitable synthesis gas for subsequent production of liquid hydrocarbons, alcohols and/or other oxidized compounds, or other synthesis gas conversion products therefrom. In terms of the stoichiometric ratio of carbon to hydrogen in lower alcohols such as methanol and ethanol and $C^{5+}$ hydrocarbons, the dry feedstock may have a stoichiometric excess of carbon relative to hydrogen. Thus water, either trapped in the feedstock or in the form of superheated steam, or both, can serve to provide additional hydrogen to maximize subsequent production of synthesis gas conversion products. In embodiments, prior to mixing, the feedstock is relatively dry, and sufficient water is provided by combining superheated steam with the dried feedstock material in mixing apparatus 300, as discussed hereinbelow.

In embodiments, from about 0.14 kilograms (0.3 pounds) to about 0.32 kilograms (0.7 pounds), from about 0.14 kg (0.3 pounds) to about 0.23 kg (0.5 pounds) or from about 0.14 kg (0.3 pounds) to about 0.18 kg (0.4 pounds) of steam is added per pound of 'dry' feedstock comprising from about 4% to about 20% moisture by weight, from about 9% to about 18% moisture or from about 10% to about 20% moisture, to provide the reformer feed mixture that is introduced into the coiled tubes of the reformer. The reformer feed mixture can have a total water to feedstock ratio in the range of from about 0.1 to 0.5, from about 0.2 to about 0.45 or from about 0.4 to about 0.5.

Feedstock reformation carried out in the feedstock reformer is endothermic. Thus, reforming apparatus 400 comprises one or more burners 404 operable to provide the necessary heat of the pyrolysis, gasification and/or reforming reaction(s) occurring within the coiled tubes 410 by combusting fuel in the presence of oxygen.

Burners 404 are desirably positioned at or near the bottom of the reformer. Burners 404 may be positioned internal or external to firebox 407. In embodiments, burner(s) 404 are internal to firebox 407. The burner(s) 404 may be distributed substantially uniformly along the diameter of vessel 407. In embodiments, the reformer has from about 1 to about 10 burners, from about 1 to about 5 burners, or from about 1 to about 2 burners. Oxidant utilized by the burner(s) may be provided as air, enriched air, or substantially pure oxygen. For example, in the embodiment of FIG. 2, each of the burners 404 is provided with air via one or more air inlet lines 405 and fuel provided via one or more fuel inlet lines 406. The oxidant and fuel may be fed separately to each burner 404 or combined prior to entry thereto. The system can further comprise a forced draft (FD) fan 409 configured to provide air to an air preheater 413 configured to raise the temperature of the inlet air from a first temperature (e.g. ambient temperature) to a temperature in the range of from about −18° C. (0° F.) to about 399° C. (750° F.), from about 38° C. (100° F.) to about 399° C. (750° F.) or from about 316° C. (600° F.) to about 399° C. (750° F.). In embodiments, flue gas exiting steam generation apparatus 500A (discussed further hereinbelow) is utilized to heat the air upstream of burner(s) 404. The air may be preheated by heat transfer with a flue gas stream in steam generator flue gas outlet line(s) 570 exiting steam generator 501A. This flue gas may have a temperature in the range of from about 649° C. (1200° F.) to about 1260° C. (2300° F.), from about 760° C. (1400° F.) to about 1204° C. (2200° F.) or from about 871° C. (1600° F.) to about 1149° C. (2100° F.).

Fuel is provided to the one or more burners 404 via fuel inlet line(s) 406. Any fuel known in the art can be utilized. In embodiments, the fuel provided to the reformer is selected from the group consisting of methane (e.g. natural gas), synthesis gas (e.g. excess synthesis gas), tailgas (e.g. Fischer-Tropsch tailgas) and combinations thereof As discussed in detail hereinbelow, in embodiments comprising tailgas recycle line(s) 770, one or more of the burners 404 may be specially designed for burning tailgas or a mixture of tailgas with at least one other gas such as methane or synthesis gas. The amount of air combined with the fuel will be adjusted as known in the art based upon the fuel utilized and the desired temperature within the reformer. In embodiments, the reformer temperature is maintained at a temperature in the range of at least 926° C. (1700° F.), 982° C. (1800° F.), 1038° C. (1900° F.), 1093° C. (2000° F.), 1149° C. (2100° F.).

For greater energy independence of the overall system, excess synthesis gas can be made and used to run a turbine and generate electricity to power the compressors and other electrically driven devices.

Figure 2:
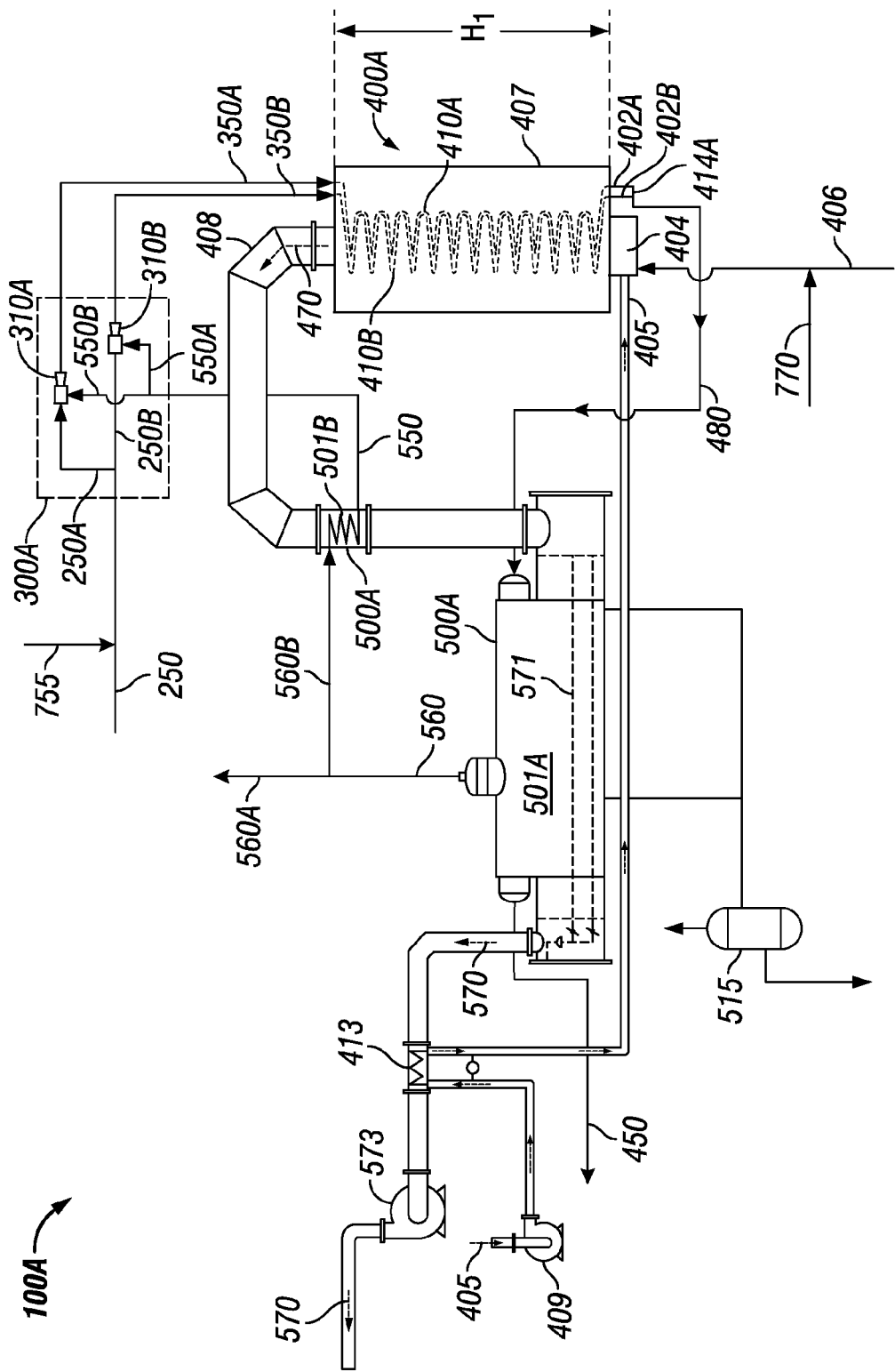
FIG. 2 is a schematic of suitable mixing apparatus, biomass reformer, and steam generation apparatus for use in the biorefinery of FIG. 1 according to an embodiment of this disclosure.

The reformer comprises one or more reformer flue gas outlet lines 470 for flue gas exiting the reformer. Desirably, reformer flue gas outlet line(s) 470 is positioned at or near the top of the reformer. In the embodiment of FIG. 2, reformer flue gas outlet lines 470 are provided a manifold 408 fluidly connecting reformer 400A with steam generation apparatus 500A. The flue gas exiting reformer 400A can have a temperature in the range of at least 926° C. (1700° F.), 982° C. (1800° F.), 1038° C. (1900° F.), 1093° C. (2000° F.), 1149° C.

(2100° F.). The pressure of the flue gas can be in the range of from about −20 inches H$_2$O to 0 inch H$_2$O; from about −16 inches H$_2$O to −2 inches H$_2$O; or from about −15 inches H$_2$O to −5 inches H$_2$O. In embodiments, the reformer is configured for operation at a pressure of greater than or equal to 5 psig (34.5 kPa), 30 psig (206.8 kPa), 40 psig (275.8 kPa), 45 psig (310.3 kPa) or 50 psig (344.7 kPa). Operation of the reformer at higher pressures may allow a reduction in the number of compression stages required upstream of the synthesis gas conversion apparatus 700 and/or a reduction in required compression horsepower.

Superheated steam from line(s) 550 carries the feedstock to the reformer. In the process of heating up the feedstock upon mixing therewith, the steam may cool to a temperature in the range of from about 150° F. (66° C.) to about 1000° F. (538° C.), from about 200° F. (93° C.) to about 750° F. (399° C.), or from about 300° F. (149° C.) to about 400° F. (204° C.). In the process of heating up the feedstock upon mixing therewith, the steam may cool to a temperature of approximately 204° C. (400° F.) as the reformer feed mixture approaches the reformer. In embodiments, the inlet temperature of the reformer feed mixture entering the reformer is at a temperature of about 204° C. (400° F.). The exit temperature of the synthesis gas leaving the reformer can be in the range of from about 870° C. (1600° F.) to about 1205° C. (2200° F.) or from about 895° C. (1650° F.) to about 930° C. (1700° F.). In embodiments, the reformer is operated at a pressure in the range of from about 135 34.5 kPa (5 psig) to about 275.8 kPa (40 psig).

Within the coiled tubes of the reformer, the carbonaceous materials in the reformer feed are anaerobically reformed with superheated steam to produce a product process gas comprising synthesis gas (hydrogen and carbon monoxide). The process gas can further comprise other components, for example, methane, carbon dioxide, and etc. Minor amounts of other ingredients may be formed. The reformer can comprise an external (see 414A in FIG. 2) or internal (see 414B in FIG. 3) manifold configured to combine the process gas from each of the coiled tubes 410 into one or more reformer process gas outlet lines 480. As indicated in the embodiment of FIG. 2, outlet lines 402 associated with each of the coiled tubes can be combined via manifold 414A to provide process gas to reformer process gas outlet line 480. In embodiments, the reformer is configured to provide temperature, pressure and residence time conditions suitable to provide a process gas comprising synthesis gas having a desired molar ratio of H$_2$ to CO. In embodiments, the reformer is configured to provide a synthesis gas having a H$_2$:CO molar ratio in the range of from about 0.7:1 to about 2:1, from about 0.7:1 to about 1.5:1 or about 1:1. In embodiments, the reformer is configured to provide a residence time within the reformer in the range of from about 0.3 s to about 3 s, from about 0.3 s to about 2 s, from about 0.3 s to about 1 s, or from about 0.4 s to about 0.6 s.

For any given feedstock, a desired composition of the resulting process gas (i.e. the proportions of hydrogen, carbon dioxide, carbon monoxide and methane) can be provided by adjusting the contact time in the reformer, the temperature at the reformer outlet, the amount of steam introduced with the feed, and to a lesser extent, the reformer pressure. In embodiments, the synthesis gas is to be utilized downstream for the production of liquid hydrocarbons via Fischer-Tropsch conversion. In embodiments, the synthesis gas is to be utilized downstream for the production of liquid hydrocarbons via Fischer-Tropsch conversion with an iron-based catalyst. In such embodiments, the system may be operated with a reformer exit temperature in the range of from about 898° C. (1650° F.) to about 926° C. (1700° F.) and a residence or contact time that is in the range of from about 0.3 seconds to about 2.0 seconds in the reformer. The contact or residence time can be calculated by dividing the internal volume of the reformer by the flow rate of the process gas exiting the reformer.

Mixing Apparatus 300. As indicated in FIG. 1, the biorefinery of this disclosure further comprises mixing apparatus 300 upstream of reformer 400. Mixing apparatus 300 is configured to combine feedstock introduced thereto via feedstock inlet line 250 with superheated steam introduced thereto via superheated steam line 550. As discussed further hereinbelow, the feedstock can be provided via feedstock handling and/or drying apparatus 200 positioned upstream of mixing apparatus 300. As discussed further hereinbelow, superheated steam can be provided via steam generation apparatus 500 configured to utilize the heat from the reformer flue gas and/or the reformer product gas to produce superheated steam from boiler feed water (BFW).

As depicted in the embodiment of FIG. 2, mixing apparatus 300A can comprise one or more mixers 310 (two mixers, 310A and 310B, indicated in FIG. 2) configured to combine superheated steam with feedstock material. Feedstock can be introduced into the mixing apparatus via one or more feedstock inlet lines 250. The feedstock comprises at least one carbonaceous material. In embodiments, the feedstock comprises biomass. The feedstock can comprise, by way of non-limiting examples, lignite, coal, red cedar, southern pine, hardwoods such as oak, cedar, maple and ash, bagasse, rice hulls, rice straw, weeds such as kennaf, sewer sludge, motor oil, oil shale, creosote, pyrolysis oil such as from tire pyrolysis plants, used railroad ties, dried distiller grains, corn stalks and cobs, animal excrement, straw, or some combination thereof. The hydrogen and oxygen content for the various materials differ and, accordingly, operation of the system (e.g. amount of superheated steam combined with the feedstock in the mixing apparatus, the reformer temperature and pressure, the reformer residence time) can be adjusted as known in the art to provide a process gas comprising synthesis gas having a suitable molar ratio of H$_2$:CO for a desired subsequent synthesis conversion application. The feedstock introduced into the mixing apparatus can have an average particle size in the range of from about 3.9E-5 inch (0.0001 cm) to about 1 inch (2.54 cm), from about 0.01 inch (0.0254 cm) to about 0.5 inch (1.27 cm) or from about 0.09 inch (0.24 cm) to about 0.2 inch (0.508 cm). In embodiments, the feedstock introduced into the mixing apparatus has an average particle size of less than about 1 inch (2.54 cm), less than about 0.5 inch (1.27 cm) or less than about 3/16 inch (0.48 cm). The feedstock introduced into the mixing apparatus can have a moisture content in the range of from about 4 weight percent to about 20 weight percent, from about 5 weight percent to about 20 weight percent, from about 10 weight percent to about 20 weight percent or from about 5 weight percent to about 18 weight percent. As discussed further hereinbelow and mentioned hereinabove, a system of this disclosure can further comprise, upstream of the mixing apparatus and connected therewith via one or more lines 250, feedstock handling and/or drying apparatus 200.

Within the mixing apparatus 300, feedstock is combined with superheated steam to provide a reformer feed mixture. In the embodiment of FIG. 2, feedstock in line 250 is divided via lines 250A and 250B and introduced into mixers 310A and 310B respectively. Superheated steam, which may be produced via steam generation apparatus 500 as further described hereinbelow, is introduced via superheated steam lines 550, 550A and 550B to mixing apparatus 300A. In embodiments, one or more spent catalyst recycle lines 755 is configured to directly or indirectly recycle at least a portion of a catalyst/conversion product (e.g. catalyst/wax or catalyst/alcohol) stream separated from the conversion product within synthesis gas conversion apparatus 700 to the reformer, as discussed further hereinbelow. In embodiments, the mixing apparatus is configured to combine the feedstock in feedstock line 250 with superheated steam having a temperature in the range of from about 400° F. (204.4° C.) to about 1000° F. (537.8° C.), from about 600° F. (315.6° C.) to about 950° F. (510° C.) or from about 400° F. (204.4° C.) to about 900° F. (482.2° C.) and/or a pressure in the range of from about 150 psig (1034.2 kPa) to about 400 psig (2757.9 kPa), from about 200 psig (1378.9 kPa) to about 375 psig (2585.5 kPa) or from about 250 psig (1723.7 kPa) to about 350 psig (2413.2 kPa). In embodiments, a system of this disclosure further comprises steam generation apparatus 500 configured to provide superheated steam for introduction into mixing apparatus 300 as further described hereinbelow.

In the embodiment of FIG. 2, superheated steam is introduced into each of the mixers 310A and 310B, respectively, via superheated steam lines 550A and 550B. The reformer feed mixture comprising feedstock and steam is introduced into the reformer via one or more reformer inlet lines 350. The feedstock/steam mixture from each mixer 310 may be introduced into a coiled tube 410. For example, in the embodiment of FIG. 2, feedstock/steam exiting mixers 310A and 310B via lines 350A and 350B, respectively, are introduced into coiled tubes 410A and 410B, respectively. In the embodiment of FIG. 3, the feedstock/steam mixture exiting mixing vessel 310C of system 100B is introduced via line 350, reformer feed distributor 412 and feed inlet lines 350A and 350B into coiled tubes 410A and 410B, respectively. Other combinations of number of mixers, manifolding of the outlets thereof, and distributors are envisioned and not beyond the scope of this disclosure.

As indicated in FIG. 3, the mixing vessel 310C can be a cylindrical vessel having a conical bottom 320. In embodiments, superheated steam is introduced at or near the bottom or into a conical section 320 at or near the bottom of the mixer. Feedstock may be introduced, in embodiments, at or near the top of the mixer. In embodiments, the mixture exits out the bottom of the mixing vessel.

In embodiments, the mixing vessel(s) (310A/310B/310C) are pressure vessels configured for operation at a pressure in the range of from about 5 psig (34.5 kPa) to about 50 psig (344.7 kPa), from about 30 psig (206.8 kPa) to about 50 psig (344.7 kPa), from about 45 psig (310.3 kPa) to about 50 psig (344.7 kPa), or configured for operation at or greater than about 30 psig (206.8 kPa), 45 psig (310.3 kPa) or 50 psig (344.7 kPa). In embodiments, the mixing vessels are configured for operation at a temperature in the range of from about a temperature in the range of from about 150° F. (66° C.) to about 1000° F. (538° C.), from about 200° F. (93° C.) to about 750° F. (399° C.), or from about 300° F. (149° C.) to about 400° F. (204° C.).

The mixing apparatus may be configured to provide a reformer feed mixture by combining from about 0.3 pound of steam per pound of feedstock to about 0.4, 0.5, 0.6, 0.7, 0.8, 0.9 or 1 pound of superheated steam per pound of feedstock. In embodiments, the mixing apparatus is configured to provide a reformer feed mixture by combining less than or equal to about 1 pound of superheated steam per pound of feedstock.

As indicated in FIG. 3 and discussed further hereinbelow, a portion of the saturated steam exiting the steam generator via one or more steam generator steam outlet line(s) 560 can be sent via one or more line(s) 560A and 560C to an excess steam condenser 516. Condensate from excess steam condenser 516 can be combined with condensate from elsewhere in the system (for example, with condensate in condensate outlet line 282 from a dryer air preheater of feed handling and/or drying apparatus 200, as discussed further hereinbelow). Condensate can be collected for disposal and/or recycle and reuse via line 283.

Steam Generation Apparatus 500. The biorefinery disclosed herein further comprises steam generation apparatus 500 configured to provide superheated steam for reforming feedstock within reformer 400/400A/400B. As depicted in the embodiment of FIG. 1, water (e.g. boiler feed water or BFW) is introduced into steam generation apparatus 500 via one or more BFW inlet lines 580, 'hot' reformer flue gas is introduced into steam generation apparatus 500 via one or more reformer flue gas outlet lines 470, 'hot' product process gas is introduced into steam generation apparatus 500 via one or more reformer process gas outlet lines 480, superheated steam exits steam generation apparatus 500 via one or more superheated steam outlet lines 550, saturated steam exits steam generation apparatus 500 via one or more steam generator steam outlet lines 560, 'cool' flue gas exits steam generation apparatus 500 via one or more steam generator flue gas outlet lines 570 and 'cool' process gas exits steam generation apparatus 500 via one or more steam generator process gas outlet lines 450.

Description of a suitable steam generation apparatus will now be made with reference to FIG. 2. In the embodiment of FIG. 2, steam generation apparatus 500A comprises reformer flue gas and reformer effluent steam generator 501A and steam superheater 501B. Reformer flue gas and reformer effluent steam generator 501A is configured to produce saturated steam by heat transfer from the 'hot' reformer effluent process gas and the 'warm' reformer flue gas exiting steam superheater 501B. Reformer effluent process gas is introduced into reformer flue gas and reformer effluent steam generator 501A via reformer process gas outlet line(s) 480. The 'hot' process gas introduced into reformer flue gas and reformer effluent steam generator 501A via reformer process gas outlet line(s) 480 may have a temperature in the range of from about 870° C. (1600° F.) to about 1205° C. (2200° F.) or from about 895° C. (1650° F.) to about 930° C. (1700° F.). In embodiments, the 'hot' process gas has a pressure in the range of from about 34.5 kPa (5 psig) to about 275 KPa (40 psig). Within reformer flue gas and reformer effluent steam generator 501A, steam is commonly generated from the flue gas and the process gas, although the two gases are not mixed. 'Cool' reformer process gas leaves reformer flue gas and reformer effluent steam generator 501A via steam generator process gas outlet line(s) 450. The 'cool' process gas exiting reformer flue gas and reformer effluent steam generator 501A via steam generator process gas line(s) 450 may have a temperature in the range of from about 400° C. (752° F.) to about 800° C. (1472° F.), from about 400° C. (752° F.) to about 600° C. (1112° F.) or about 400° C. (752° F.) and/or a pressure in the range of from about 5 psig (34.5 kPa) to about 50 psig (344.7 kPa), from about 10 psig (68.9 kPa) to about 40 psig (275.8 kPa) or from about 20 psig (137.9 kPa) to about 30 psig (206.8 kPa).

Reformer flue gas is introduced into reformer flue gas and reformer effluent steam generator 501A via reformer flue gas outlet line(s) 470. The 'hot' flue gas introduced into reformer flue gas and reformer effluent steam generator 501A via reformer flue gas outlet line(s) 470 may have a temperature in the range of from about 530° F. (276.7° C.) to about 1500° F. (815.6° C.), from about 530° F. (276.7° C.) to about 1200° F.

(648.9° C.) or about 530° F. (276.7° C.) and/or a pressure in the range of from about −20 inches $H_2O$ to 0 inches $H_2O$; from about −15 inches $H_2O$ to about −5 inches $H_2O$; or from about −10 inches $H_2O$ to about −5 inches $H_2O$. As depicted in FIG. 2, in embodiments the reformer flue gas passes through steam superheater 501B, as discussed further hereinbelow, prior to introduction into reformer flue gas and reformer effluent steam generator 501A. In such instances, the 'warm' flue gas introduced into the reformer flue gas and reformer effluent steam generator 501A may have a temperature in the range of from about 1350° F. (732.2° C.) to about 2050° F. (1121.1° C.), from about 1450° F. (787.8° C.) to about 1950° F. (1065.6° C.) or from about 1350° F. (732.2° C.) to about 1850° F. (1010° C.) and/or a pressure in the range of from about −20 inches $H_2O$ to 0 inch $H_2O$; −16 inches $H_2O$ to −5 inches $H_2O$; −15 inches $H_2O$ to 5 inches $H_2O$. In embodiments, the temperature of the 'warm' flue gas is about 150 degrees less than that of the 'hot' flue gas, i.e. the flue gas temperature drop across 501B is in the range of from about 130-170 degrees, from about 140-160 degrees, or about 150 degrees.

'Cool' reformer flue gas leaves reformer flue gas and reformer effluent steam generator 501A via steam generator flue gas outlet line(s) 570. The 'cool' flue gas exiting reformer flue gas and reformer effluent steam generator 501A via steam generator flue gas outlet line(s) 570 may have a temperature in the range of from about 50° F. (10° C.) to about 400° F. (204.4° C.), from about 200° F. (93.3° C.) to about 400° F. (204.4° C.) or about 400° F. (204.4° C.) and/or a pressure in the range of from about −20 inches $H_2O$ to about 20 inches $H_2O$; from about −16 inches to about 20 inches $H_2O$; or from about −15 inches $H_2O$ to about −10 inches $H_2O$. Induced draft (ID) fan 573 can serve to draw 'cool' reformer flue gas exiting reformer flue gas and reformer effluent steam generator 501A via steam generator flue gas outlet line(s) 570 through air preheater 413, discussed hereinabove. Heat transfer to the air within air preheater 413 may provide a 'cold' flue gas for use elsewhere in the system, for example in a dryer air heater of a feed handling and/or drying apparatus 200, as further discussed hereinbelow. The 'cold' flue gas passing out of air preheater 413 in line(s) 570 may have a temperature in the range of from about −18° C. (0° F.) to about 399° C. (750° F.), from about 38° C. (100° F.) to about 399° C. (750° F.) or from about 316° C. (600° F.) to about 399° C. (750° F.) and/or a pressure in the range of from about −20 inches $H_2O$ to about 20 inches $H_2O$; from about −16 inches to about 20 inches $H_2O$; or from about −15 inches $H_2O$ to about −10 inches $H_2O$.

One or more steam generator steam outlet lines 560 carries steam (e.g. saturated steam) from reformer flue gas and reformer effluent steam generator 501A. A portion of the saturated steam may be directed via one or more steam export lines 560A for export to another apparatus or use elsewhere in the system. As indicated in the embodiment of FIG. 2, all or a portion of the saturated steam produced in reformer flue gas and reformer effluent steam generator 501A can be directed to steam superheater 501B configured to produce superheated steam. Steam superheater 501B is configured to provide superheated steam at a temperature in the range of from about 400° F. (204.4° C.) to about 1000° F. (537.8° C.), from about 600° F. (315.6° C.) to about 950° F. (510° C.) or from about 400° F. (204.4° C.) to about 900° F. (482.2° C.) and/or a pressure in the range of from about 150 psig (1034.2 kPa) to about 400 psig (2757.9 kPa), from about 200 psig (1379 kPa) to about 375 psig (2585.5 kPa) or from about 250 psig (1723.7 kPa) to about 350 psig (2413.2 kPa). In embodiments, steam superheater 501B operates via heat transfer from the 'hot' reformer flue gas in reformer flue gas outlet line(s) 470. Steam superheater 501B may be configured on a manifold or header 408 comprising reformer flue gas outlet(s) 470. As mentioned hereinabove, the 'warm' flue gas exiting the steam superheater may have a temperature in the range of from about 1500° F. (815.6° C.) to about 2200° F. (1204.4° C.), from about 1600° F. (871.1° C.) to about 2150° F. (1176.7° C.) or from about 1600° F. (871.1° C.) to about 2100° F. (1148.9° C.) and/or a pressure in the range of from about −20 inches $H_2O$ to 0 inches $H_2O$; −16 inches $H_2O$ to −5 inches $H_2O$; −15 inches $H_2O$ to 5 inches $H_2O$. As discussed hereinabove, superheated steam exiting steam superheater 501B can be introduced into the mixing apparatus 300 via one or more superheated steam lines 550.

Reformer flue gas and reformer effluent steam generator 501A may, as known in the art, be associated with one or more blowdown drums 515 configured to purge water off and control the solids level within reformer flue gas and reformer effluent steam generator 501A.

Description of a suitable steam generation apparatus according to another embodiment of this disclosure will now be made with reference to FIG. 3. In the embodiment of FIG. 3, the steam generation apparatus 500B comprises flue gas steam generator 501A" and reformer effluent steam generator 501A'. In the embodiment of FIG. 3, 'hot' reformer effluent process gas exiting reformer 400B via reformer process gas outlet lines 480 passes through reformer effluent steam generator 501A', configured for transfer of heat from the 'hot' reformer process gas to BFW introduced thereto via BFW inlet line 580. 'Cool' process gas exiting reformer effluent steam generator 501A' via steam generator process gas outlet line 450 may have a temperature in the range of from about 752° F. (400° C.) to about 1472° F. (800° C.), from about 752° F. (400° C.) to about 1112° F. (600° C.) or about 752° F. (400° C.) and/or a pressure in the range of from about 5 psig (34.5 kPa) to about 50 psig (344.7 kPa), from about 10 psig (68.9 kPa) to about 40 psig (275.8 kPa) or from about 20 psig (137.9 kPa) to about 30 psig (206.8 kPa).

Reformer flue gas outlet line(s) 470 may fluidly connect reformer 400B with steam superheater 501B'. As discussed in regard to FIG. 2, steam superheater 501B' is configured to produce superheated steam having a temperature in the range of from about 400° F. (204.4° C.) to about 1000° F. (537.8° C.), from about 600° F. (315.6° C.) to about 950° F. (510° C.) or from about 900° F. (482.2° C.) and/or a pressure in the range of from about 150 psig (1034.2 kPa) to about 400 psig (2757.9 kPa), from about 200 psig (1379 kPa) to about 375 psig (2585.5 kPa) or from about 250 psig (1723.7 kPa) to about 350 psig (2413.2 kPa). One or more superheated steam lines 550 are configured to carry the superheated steam from steam superheater 501B' to mixing vessel(s) 310C. The 'warm' flue gas exiting steam superheater 501B' has a temperature in the range of from about 1350° F. (732.2° C.) to about 2050° F. (1121.1° C.), from about 1450° F. (787.8° C.) to about 1950° F. (1065.6° C.) or about 1850° F. (1010° C.) and/or a pressure in the range of from about −20 inches $H_2O$ to 0 inch $H_2O$; −16 inches $H_2O$ to −5 inches $H_2O$; −15 inches $H_2O$ to 5 inches $H_2O$ and passes through flue gas steam generator 501A", configured for transferring heat from the 'warm' reformer flue gas to the steam in line 580A. One or more lines 560 are configured to carry saturated steam exiting flue gas steam generator 501A".

One or more steam generator flue gas outlet lines 570 are configured to carry 'cool' flue gas from flue gas steam generator 501A". As mentioned hereinabove, the 'cool' flue gas exiting flue gas steam generator 501A" can have a temperature in the range of from about 50° F. (10° C.) to about 400° F. (204.4° C.), from about 200° F. (93.3° C.) to about 400° F.

(204.4° C.) or about 400° F. (204.4° C.) and/or a pressure in the range of from about −20 inches H$_2$O to about 20 inches H$_2$O; from about −16 inches to about 20 inches H$_2$O; or from about −15 inches H$_2$O to about −10 inches H$_2$O. As discussed with regard to FIG. 2, the 'cool' flue gas in steam generator flue gas outlet line 570 may be used to heat combustion air in combustion air preheater 413. Combustion air preheater 413 may be configured to heat air introduced thereto via FD fan 406 and one or more air inlet lines 405 from a first lower temperature (e.g. ambient temperature) to a second higher temperature in the range of from about from about 38° C. (100° F.) to about 399° C. (750° F.), from about 316° C. (600° F.) to about 399° C. (750° F.) or about 399° C. (750° F.) for introduction into the reformer burner(s). 'Cold' flue gas exiting air preheater 413 may have a temperature in the range of from about −18° C. (0° F.) to about 399° C. (750° F.), from about 38° C. (100° F.) to about 399° C. (750° F.) or from about 316° C. (600° F.) to about 399° C. (750° F.) and/or a pressure in the range of from about −20 inches H$_2$O to about 20 inches H$_2$O; from about −16 inches to about 20 inches H$_2$O; or from about −15 inches H$_2$O to about −10 inches H$_2$O. The 'cold' flue gas may be utilized elsewhere in the refinery, for example, in a dryer air heater of a feed handling and/or drying apparatus, as further discussed hereinbelow.

It will be apparent to those of skill in the art that flue gas steam generator 501A" and reformer effluent steam generator 501A' of the embodiment of FIG. 3 may be combined within a single vessel as indicated in the embodiment of FIG. 2.

Synthesis Gas Clean-up and Conditioning Apparatus 600. The biorefinery disclosed herein can further comprise synthesis gas cleanup and/or conditioning apparatus 600 configured to prepare the synthesis gas for introduction into synthesis gas conversion apparatus 700. As indicated in FIG. 1, synthesis gas cleanup and/or conditioning apparatus 600 is located downstream of reforming apparatus 400 and steam generation apparatus 500. Thus, the biorefinery is configured such that synthesis gas produced in the reforming apparatus 400 is, after passing through steam generation apparatus 500, introduced into synthesis gas cleanup and/or conditioning apparatus 600.

Syngas cleanup and conditioning is a key technical barrier to the commercialization of biomass gasification technologies and typically has the greatest impact on the cost of clean synthesis gas. Generally, tar reforming catalysts have not demonstrated that they can clean and condition raw synthesis gas to meet the strict quality standards mandated for economically feasible downstream production of products such as mixed alcohols and liquid hydrocarbons therefrom. The synthesis gas cleanup and conditioning apparatus disclosed herein can be utilized to overcome some of these deficiencies.

Synthesis gas cleanup and/or conditioning apparatus 600 is configured to remove undesirables, indicated to be removed via lines 660A and 660B in FIG. 1, from the synthesis gas produced in the reformer (i.e. to 'cleanup' the synthesis gas) and provide a synthesis gas having a desired composition for a particular downstream application (i.e. to 'condition' the synthesis gas). For example, synthesis gas cleanup and/or conditioning apparatus 600 can be configured to remove one or more undesirable components including, but not limited to, ash, carbon dioxide, tar, methane, sulfur compounds, (excess) hydrogen and aromatics from the reformer product, providing a cleaned up and conditioned synthesis gas having a desired molar ratio of hydrogen to carbon monoxide and acceptable levels of other components, including but not limited to, carbon dioxide, ash, aromatics, methane, tars, carbon dioxide and etc.

In embodiments, synthesis gas cleanup and/or conditioning apparatus 600 comprises any combination of units known in the art to be suitable for cleaning and conditioning synthesis gas for downstream Fischer-Tropsch production of liquid fuels. In embodiments, synthesis gas cleanup and/or conditioning apparatus 600 comprises one or more units selected from ash removal apparatus, tar removal apparatus, aromatics removal units, hydrogen adjustment units, carbon dioxide removal units, and combinations thereof In embodiments, synthesis gas cleanup and/or conditioning apparatus 600 comprises a nickel dual fluid bed apparatus as described in U.S. patent application Ser. No. 12/691,297, which is hereby incorporated herein in its entirety for all purposes not contrary to this disclosure.

Figure 4:
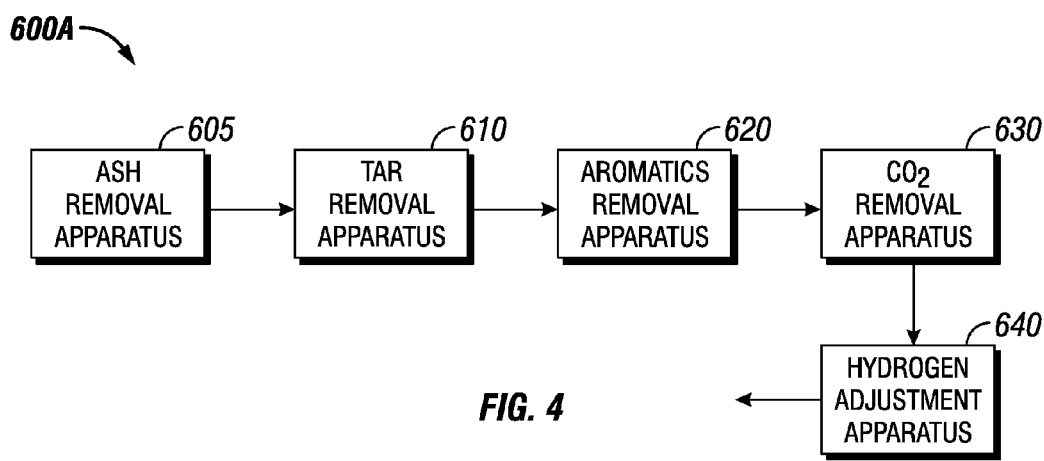
FIG. 4 is a schematic of a synthesis gas cleanup and/or conditioning apparatus suitable for use in the biorefinery of FIG. 1 according to an embodiment of this disclosure.

FIG. 4 is a schematic of a synthesis gas cleanup and/or conditioning apparatus 600A suitable for use in a biorefinery according to embodiments of this disclosure. As indicated in the embodiment of FIG. 4, synthesis gas cleanup and/or conditioning apparatus can comprise one or more of ash removal apparatus 605, tar removal apparatus 610, aromatics removal apparatus 620, carbon dioxide removal apparatus 630 and hydrogen adjustment apparatus 640. It is to be understood that a single apparatus or type of apparatus may be configured to remove more than one undesirable compound. For example, an aromatics removal unit may also serve as a tar removal unit (e.g. a TEG unit) and/or a tar removal unit may also serve as an ash removal unit (e.g. a venturi scrubber). It is also noted that the order of the apparatus depicted in FIG. 4 may be rearranged as known in the art depending on the specific units incorporated into the system.

In embodiments, synthesis gas cleanup and/or conditioning apparatus 600 comprises ash removal apparatus 605. The ash removal apparatus 605 is configured to remove ash from the synthesis gas produced in the reformer. As some of the carbonaceous material used as feedstock for the production of synthesis gas is not carbonaceous, the ash removal apparatus may serve to remove such non-carbonaceous materials, such as phosphates and minerals therefrom. Desirably, ash removal apparatus 605 reduces the level of ash in the synthesis gas to less than 12 weight percent ash, less than 6 weight percent ash or less than 2.3 weight percent ash. In embodiments, ash removal apparatus 605 comprises one or more units selected from cyclones, baghouses, and scrubbers (e.g. venturi scrubbers or quench units). In embodiments, ash removal apparatus 605 comprises a first cyclone configured to separate particles having an average particle size of more than 1 μm, 100 μm, or 10000 μm from the synthesis gas. In embodiments, ash removal apparatus 605 comprises a second cyclone configured to remove particles having an average particle size of larger 1 μm, 100 μm, or 10000 μm from the synthesis gas exiting a first cyclone.

As depicted in FIG. 4, the synthesis gas cleanup and/or conditioning apparatus may comprise tar removal apparatus 610 and/or aromatics removal apparatus 620. Any tar removal apparatus known in the art may be utilized to reduce the level of tar in the synthesis gas. Desirably, tar removal apparatus is configured to reduce the tar level in the synthesis gas to less than 1.0 weight percent tar, less than 0.1 weight percent tar, less than 0.01 weight percent or less than 0.002 weight percent tar. In embodiments, the tar level in the synthesis gas is reduced to less than 200 mg/L. In embodiments, the synthesis gas cleanup and/or conditioning apparatus comprises a venturi scrubber, for example downstream of one or more cyclone(s) or baghouses of an ash removal apparatus 605. The venturi scrubber may be configured to wash out water-soluble hydrocarbons, tars, aromatics such as benzene and any remaining ash (e.g. fines that may have escaped upstream ash separation via ash removal apparatus 605) from the synthesis gas. The venturi scrubber may be configured for operation with a wash liquid. The wash liquid may be water. Thus, a venturi scrubber may serve as ash removal apparatus 605, a tar removal apparatus 610, and/or an aromatics removal apparatus 620 (e.g. a benzene recovery unit) in a single unit. In embodiments, the synthesis gas cleanup and/or conditioning apparatus comprises one or more triethylene glycol units (TEG units) configured for solvent extraction of tars and aromatics from the synthesis gas. In embodiments, one or more TEG units are positioned downstream of one or more cyclones of ash removal apparatus 605 and downstream of a venturi scrubber ash removal unit 605/tar removal unit 610. The TEG unit may serve as tar removal unit 610 and aromatics removal unit 620 in a single apparatus. In embodiments, the TEG unit(s) removes remaining tars (e.g. heavy tars) from the synthesis gas, reducing the tar level in the synthesis gas to less than 1.0 weight percent, less than 0.1 weight percent, or less than 0.01 weight percent. In embodiments, the TEG unit(s) reduces the BTEX level in the synthesis gas to less than 0.5 weight percent, less than 0.05 weight percent, or less than 0.005 weight percent. In embodiments, the BTEX level is reduced to less than or about 60, 50 or 45 mg/L.

As indicated in FIG. 4, synthesis gas cleanup and/or conditioning apparatus 600A can comprise carbon dioxide removal apparatus 630. In embodiments, the carbon dioxide removal apparatus reduces the carbon dioxide content of the synthesis gas to less than 10 weight percent, less than 1.0 weight percent or less than 0.1 weight percent. Any apparatus known in the art for the removal of carbon dioxide from a synthesis gas stream may be implemented in the biorefinery of this disclosure. In embodiments, the synthesis gas cleanup and/or conditioning apparatus comprises an acid gas removal unit (AGRU) configured to remove carbon dioxide from synthesis gas introduced thereto. In embodiments, the synthesis gas cleanup and/or conditioning apparatus comprises an amine unit configured to remove hydrogen sulfide and carbon dioxide from synthesis gas introduced thereto.

The amine unit(s) removes carbon dioxide from the syngas. In embodiments, a pressure swing adsorbent (PSA) unit, discussed below in connection with hydrogen removal, could be used instead of an amine scrubber to remove the carbon dioxide. In an amine unit, the synthesis gas is scrubbed with an amine-based solvent in an absorption column. The solvent is regenerated in a second column thereby releasing a high purity $CO_2$ product.

The carbon dioxide removal apparatus 630 serves as one point source of carbon dioxide sequestration provided by the disclosed biorefinery. The carbon dioxide removed from the synthesis gas may be sequestered and sold, for example, for use in enhanced oil recovery (EOR), as known in the art. Sulfur compounds that may be removed in the carbon dioxide removal apparatus (e.g. via one or more AGRU's) may be used to produce valuable commodities such as, but not limited to, fertilizer and sulfuric acid. Sequestration of carbon dioxide in this manner is environmentally-friendly, as it allows for a substantial reduction in the amount of carbon dioxide, a 'greenhouse' gas, that is ultimately disposed via undesirable venting to the atmosphere.

As indicated in FIG. 4, the synthesis gas cleanup and/or conditioning apparatus can comprise hydrogen adjustment apparatus 640. Depending on the ultimate application intended for the synthesis gas, adjustment of the hydrogen content in the synthesis gas may be desirable. For example, for use in Fischer-Tropsch production of liquid hydrocarbons via Fischer-Tropsch synthesis over an iron-based catalyst, it may be desirable to remove hydrogen from the synthesis gas upstream of a Fischer-Tropsch synthesis reactor in order to reduce the molar ratio of hydrogen to carbon monoxide (e.g. to provide a hydrogen to carbon monoxide molar ratio of about 1:1). Desirably, the reformer 400 is operated with such a composition of feed (i.e. moisture and/or steam content) and at appropriate temperature, pressure, and residence time that the synthesis gas produced therein has the desired molar ratio of hydrogen to carbon monoxide. However, in embodiments, subsequent hydrogen adjustment may be necessary to provide a desired ratio for introduction into subsequent Fischer-Tropsch processes.

In embodiments, hydrogen adjustment apparatus 640 is configured to increase the molar ratio of hydrogen to carbon monoxide in the synthesis gas (i.e. to increase the hydrogen content). In such embodiments, hydrogen adjustment apparatus 640 may comprise a water gas shift reactor (WGSR) configured to produce additional hydrogen and carbon dioxide from water and some of the carbon monoxide in the synthesis gas, as known in the art. In such embodiments, it may be desirable to position the WGSR upstream of the carbon dioxide removal apparatus 630 in order to allow subsequent removal of the carbon dioxide produced in the WGSR. In embodiments, hydrogen adjustment apparatus 640 is configured to decrease the molar ratio of hydrogen to carbon monoxide in the synthesis gas (i.e. to decrease the hydrogen content). In such embodiments, the hydrogen adjustment apparatus 640 may comprise a hydrogen membrane or pressure swing absorber (PSA), as known in the art, configured to remove hydrogen from the synthesis gas.

In embodiments, hydrogen adjustment apparatus comprises at least one PSA, as mentioned hereinabove with regard to carbon dioxide removal. In embodiments incorporating a PSA, the synthesis gas can be compressed in one or more compressors, for example to a pressure of between 6895 KPa (1000 psi) and 16,547 KPa (2400 psi), and the resulting compressed synthesis gas stream fed to the PSA unit(s) configured to remove a portion of the hydrogen from the synthesis gas.

Pressure swing adsorption (PSA) is an adiabatic process and is applied for partial hydrogen removal from synthesis gas by removing some of the hydrogen by adsorption through suitable adsorbents in fixed beds contained in pressure vessels under high pressure. Regeneration of adsorbents is accomplished by countercurrent depressurization and by purging at low pressure with previously recovered hydrogen gas. To obtain a continuous flow of product, a minimum of two adsorbers may be utilized, such that at least one adsorber is receiving feed syngas. Simultaneously, the subsequent steps of depressurization, purging and repressurization back to the adsorption pressure are executed by the other adsorber(s). After such adsorbent regeneration and repressurization the adsorber is switched onto adsorption duty, whereupon another adsorber is regenerated. For removing hydrogen, the adsorbent used is generally silica gel.

An alternative type of hydrogen separator which might be used to separate a portion of the hydrogen from the synthesis gas in synthesis gas cleanup and/or conditioning 600 is a hydrogen specific permeable membrane separator.

Synthesis Gas Conversion Apparatus 700. The biorefinery of this disclosure further comprises synthesis gas conversion apparatus 700. As depicted in FIG. 1, synthesis gas conversion apparatus 700 is located downstream of synthesis gas cleanup and/or conditioning apparatus 600. In embodiments, synthesis gas conversion apparatus 700 is any suitable synthesis gas conversion apparatus known in the art for the production of valuable products (e.g. liquid hydrocarbons, ethanol, methanol, mixed alcohols) from synthesis gas. By way of nonlimiting examples, the synthesis gas conversion apparatus can comprise at least one selected from Fischer-Tropsch reactors, alcohol synthesis reactors and microbial alcohol synthesis reactors. In embodiments, synthesis gas conversion apparatus 700 comprises a Fischer-Tropsch reactor configured for the production of liquid hydrocarbons from synthesis gas. In embodiments, the Fischer-Tropsch reactor configured for the production of liquid hydrocarbons from synthesis gas is configured to operate with and/or contains an iron-based FT catalyst or a cobalt-based FT catalyst. In embodiments, the FT catalyst is an iron-based catalyst formed as described in or having the composition of FT catalyst described in U.S. Pat. No. 5,504,118 and/or U.S. patent application Ser. Nos. 12/189,424; 12/198,459; 12/207,859; 12/474,552; and/or 12/790,101, the disclosures of each of which are hereby incorporated herein in their entirety for all purposes not contrary to this disclosure.

As indicated in FIG. 1, one or more conversion product outlet lines 750 are configured for the removal of conversion product from synthesis gas conversion apparatus 700. In embodiments, the conversion product comprises primarily liquid hydrocarbons. In embodiments, the conversion product comprises primarily alcohols. In embodiments, the conversion product comprises primarily Fischer-Tropsch hydrocarbons having five or more carbon atoms (i.e. $C^{5+}$ hydrocarbons). In embodiments, a spent catalyst recycle line 755 is configured to directly or indirectly recycle at least a portion of a catalyst/conversion product (e.g. catalyst/wax or catalyst/alcohol) stream separated from the conversion product within synthesis gas conversion apparatus 700 to the reformer. For example, spent catalyst recycle line 755 may fluidly connect synthesis gas conversion apparatus 700 with feedstock inlet line 250 such that the catalyst/product may be combined with superheated steam in mixing apparatus 300 and subsequently introduced into the reformer. At the high temperatures of operation of the reformer, even long chain hydrocarbons (i.e. wax) in a conversion product can be easily converted into additional synthesis gas. In this manner, the hydrocarbons and/or other conversion products in the catalyst/product can be converted to additional synthesis gas, thus improving the overall liquid yields from the system. Additionally, as spent catalyst is typically sent for disposal, for example, in a landfill and since incorporation into the biorefinery of this disclosure of such a spent catalyst recycle line enables the spent catalyst to be separated in the ash (for example, via ash removal in the synthesis gas cleanup and/or conditioning apparatus), such recycle enables a reduction in the amount of waste material that must ultimately be disposed. In embodiments, the overall liquid yield from a biorefinery of this disclosure comprising a Fischer-Tropsch reactor configured for the production of liquid hydrocarbons is in the range of from about 0.5 to about 1.4 barrels, from about 0.6 to 2 barrels, or from about 0.6 to about 1.5 barrels of conversion product per dry ton of feed material. In embodiments, the overall liquid yield from a biorefinery of this disclosure is greater than or equal to about 0.4, 0.5, 0.6, 0.7 0.8, 0.9, 1.0, 1.1, 1.2, 1.3 or 1.4 barrels (16.8, 21, 25.2, 29.4, 33.6, 37.8, 42, 46.2, 50.4, 54.6, or 58.8 gallons) of Fischer-Tropsch conversion product per dry ton of feed material.

As indicated in FIG. 1, one or more tailgas outlet lines 760 are configured to remove tailgas from synthesis gas conversion apparatus 700. The tailgas can comprise carbon monoxide, hydrogen, methane, carbon dioxide and possibly other components. In the biorefinery of this disclosure, at least a portion of the tailgas produced in synthesis gas conversion apparatus 700 may beneficially be recycled via one or more tailgas recycle lines 770 to reformer 400 for use as fuel in the burner(s) thereof. In embodiments, the one or more tailgas recycle lines 770 fluidly connect the one or more tailgas outlet lines 760 with one or more of the one or more fuel inlet lines 406 feeding the one or more burners 404 configured to provide heat to the reformer. In embodiments, the one or more tailgas recycle lines 770 fluidly connect the one or more tailgas outlet lines 760 directly with one or more of the one or more burners 404. In this manner, a 'waste' stream that is generally considered of little value (i.e. tailgas) can be utilized to benefit in the disclosed biorefinery. It is envisioned that, in embodiments, the biorefinery further comprises a dedicated carbon dioxide removal apparatus such that carbon dioxide may be extracted from all or a portion of the tailgas exiting synthesis gas conversion apparatus 700 via line 760 and/or all or a portion of the tailgas recycled via tailgas recycle line(s) 770 and/or that a carbon dioxide removal apparatus 630 of synthesis gas cleanup and/or conditioning apparatus 600 is utilized to remove carbon dioxide therefrom. In this manner, the biorefinery and method of producing conversion product therefrom may be made even more 'green', by enabling sequestration of additional carbon dioxide. Accordingly, in embodiments, tailgas recycle line(s) 770 is fluidly connected with an acid gas removal unit (AGRU) configured for the removal of carbon dioxide therefrom prior to introduction of the recycle tailgas into one or more burner(s) of the reformer. In embodiments, an AGRU is positioned downstream of synthesis gas conversion apparatus 700 such that all or a portion of the tailgas exiting synthesis gas conversion apparatus 700 via tailgas outlet line(s) 760 can be introduced thereto and carbon dioxide removed therefrom. In embodiments, an AGRU positioned downstream of synthesis gas conversion apparatus 700 is configured to reduce the carbon dioxide content of the tailgas to less than 10 weight percent, less than 1.0 percent or less than 0.1 percent. In embodiments, membrane technology is utilized to remove carbon dioxide from at least a portion of the tailgas exiting the synthesis gas conversion apparatus 700 via tailgas outlet line(s) 760 and/or from at least a portion of the tailgas utilized as fuel in one or more burner(s) associated with the reformer. Such carbon dioxide removal from the tailgas can provide another point source for carbon dioxide sequestration within the disclosed biorefinery. In embodiments, at least a portion of the carbon dioxide-reduced tailgas (containing combustible material) is recycled as fuel to the reformer.

Although not specifically discussed herein, one of skill in the art would understand that various other units may be utilized in the disclosed biorefinery. For example, in embodiments, synthesis gas compression apparatus (e.g. synthesis gas booster compressor), as known in the art, is positioned upstream of synthesis gas conversion apparatus 700.

Feed Handling and/or Drying Apparatus 200. A biorefinery of this disclosure may further comprise feed handling and/or drying apparatus configured to provide feed material of a desired average particle size, composition and/or moisture content to the downstream mixing apparatus. In embodiments, the feed handling and/or drying apparatus is substantially as disclosed in U.S. Pat. No. 7,375,142, the disclosure of which is hereby incorporated herein in its entirety for all purposes not contrary to this disclosure.

Suitable feed handling and/or drying apparatus can comprise an unloading and tramp metal removal zone I, a comminuting zone II, a drying zone III, a reformer feed hopper zone, or some combination of two or more thereof. A feed handling and/or drying apparatus will now be described with reference to FIG. 5, which is a schematic of a feeding and drying apparatus 200A according to an embodiment of this disclosure. Feed handling and/or drying apparatus 200A comprises unloading and tramp metal removal zone I configured for unloading of feed material and removal of undesirables therefrom. Unloading and tramp removal zone I can comprise a truck unloading hopper 205 into which delivered feed material is deposited. Truck unloading hopper 205 may be associated with a tramp metal detector 204 configured to determine the presence or absence of undesirables such as metals in the feed material. Unloading and tramp removal zone I can further comprise a conveyor 203 configured to convey feed material onto a weigh belt feeder 206. A tramp metal separator 207 is configured to remove tramp metal and other undesirables from the feed material introduced thereto. Removed undesirables can be introduced via line 208 into and stored in a bin 209 for disposal.

Comminuting zone II can be positioned downstream of unloading and tramp removal zone I, as indicated in FIG. 4, or can be downstream of an unloading zone (i.e. in the absence of a tramp removal zone). Comminuting zone II comprises apparatus configured to comminute the feed material. In embodiments, the comminuting zone comprises at least one grinder 210. A comminuting zone II may be used depending on the consistency of the feedstock. In embodiments, the feedstock is primarily wood and/or other organic material. Grinder 210 may be used if the feedstock is clumped together, in unusually large conglomerates, or if the feedstock needs to be further ground before being dried. After the feedstock is optionally subjected to grinding, the ground material may be passed via grinder outlet line 212 into one or more grinder discharge cyclones 220 configured to separate a larger average size fraction of feed material from a smaller sized fraction. The larger sized fraction may be introduced via one or more grinder discharge cyclone outlet lines 225 into one or more dryers 260 of dryer zone III configured to reduce the moisture content of the material fed thereto. The smaller sized fraction from grinder discharge cyclone 220 may be passed via grinder discharge fines outlet line 222 and grinder discharge blower 230 into a dryer baghouse 240 of drying zone III, as further discussed hereinbelow. In embodiments, grinder discharge cyclone 220 is configured to provide solids having a particle size of greater than 3⁄16" (0.48 cm) into dryer 260 via grinder discharge cyclone outlet line 225. In embodiments, grinder discharge cyclone 220 is configured to separate solids having a particle size of less than 3⁄16" (0.48 cm) into grinder discharge fines outlet line 222. In embodiments, grinder discharge cyclone 220 is at least about 93, 94, 95, 96 or at least about 97 percent efficient.

Figure 5:
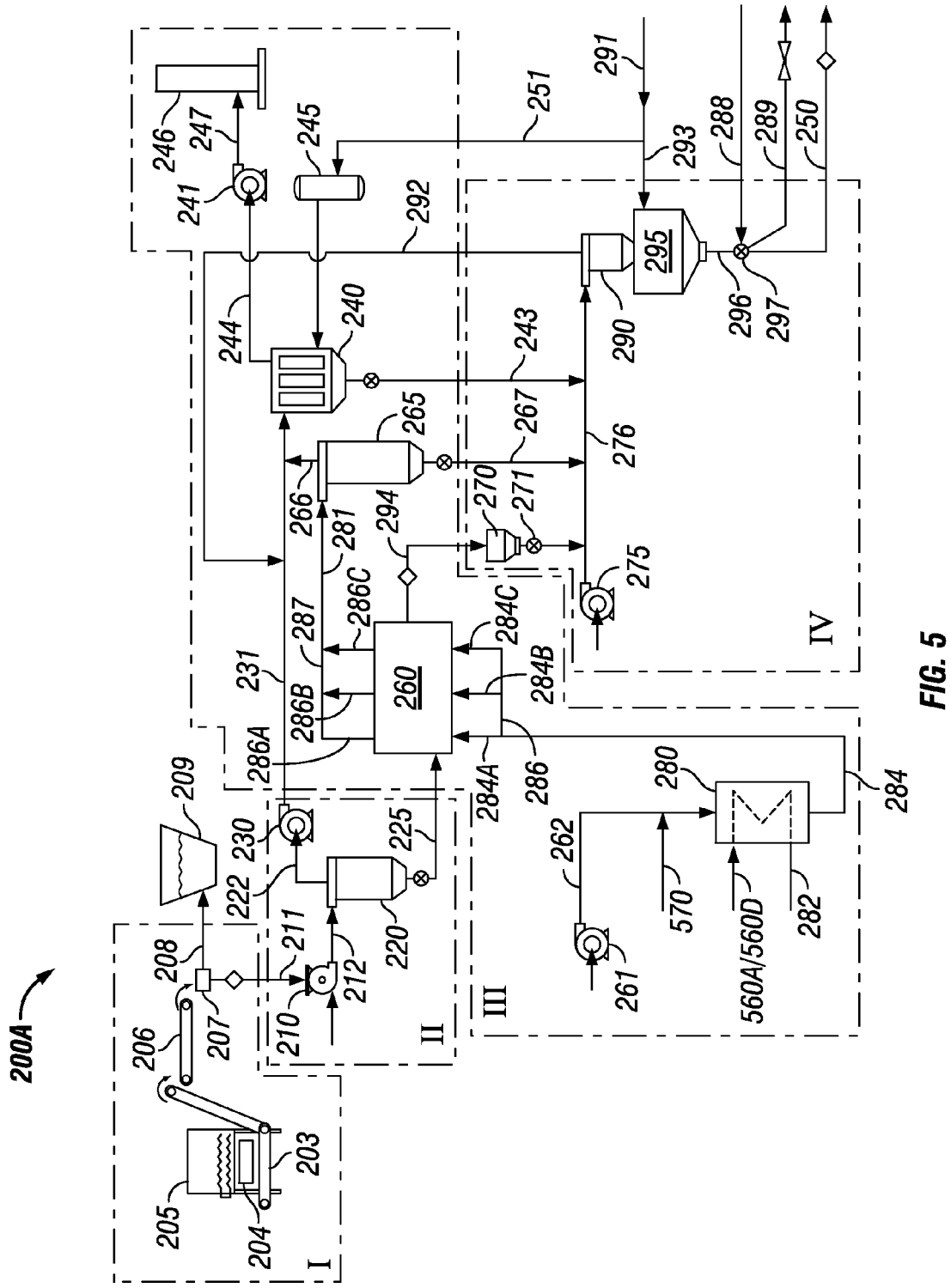
FIG. 5 is a schematic of a feedstock handling and/or drying apparatus suitable for use in the biorefinery of FIG. 1 according to an embodiment of this disclosure.

Drying zone III comprises at least one dryer 260 configured to reduce the moisture content of feed material introduced therein. In the embodiment of FIG. 5, drying zone III comprises dryer 260, dryer air heater 280, dryer cyclone 265, dryer baghouse 240, accumulator 245, dryer exhaust fan 241 and dryer stack 246. Various embodiments may comprise any combination of these components. Within drying zone III, the feedstock is dried to a moisture content in the range of from about 5% to about 20%, from about 5% to about 15% or from about 9% to about 15%. The flue gas and air fed into dryer 260 mixes with comminuted feedstock to dry it, purge it and heat it for further processing.

An air supply fan 261 is configured to introduce air via line 262 and reformer flue gas (e.g. 'cold' reformer flue gas from air preheater 413) via line 570 into dryer air heater 280. The flue gas may be added upstream of dryer air preheater 280 to prevent temperatures above 400° F. (204.4° C.) to the inlet of dryer 260, preventing fire therein. As mentioned hereinabove, the 'cold' flue gas may have a temperature in the range of from about −18° C. (0° F.) to about 399° C. (750° F.), from about 38° C. (100° F.) to about 399° C. (750° F.) or from about 316° C. (600° F.) to about 399° C. (750° F.) and/or a pressure in the range of from about −20 inches $H_2O$ to about 20 inches $H_2O$; from about −16 inches to about 20 inches $H_2O$; or from about −15 inches $H_2O$ to about −10 inches $H_2O$. In embodiments, the flue gas introduced via line 570 comprises about 80% nitrogen and 20% $CO_2$.

A portion of the effluent steam from reformer effluent and reformer flue gas steam generator 501A or from flue gas steam generator 501A" can be introduced via line 560A or 560D into dryer air preheater 280. The steam introduced into dryer air preheater 280 may have a temperature in the range of from about 150° F. (65.6° C.) to about 500° F. (260° C.), from about 250° F. (121.1° C.) to about 450° F. (232.2° C.) or from about 300° F. (148.9° C.) to about 400° F. (204.4° C.) and/or a pressure in the range of from about 70 psig (482.6 kPa) to about 300 psig (2068.4 kPa), from about 150 psig (1034.2 kPa) to about 300 psig (2068.4 kPa) or from about 250 psig (1723.7 kPa) to about 300 psig (2068.4 kPa). Condensate outlet line 282 is configured for removal of condensate from air dryer 280. The pressure of the condensate may be reduced downstream of the air dryer 280 and the condensate combined as indicated in FIG. 3 with condensate from excess steam condenser 516. Heated air exiting dryer air heater 280 via heated air line 284 may have a temperature in the range of from about −18° C. (0° F.) to about 204° C. (400° F.), from about −18° C. (0° F.) to about 149° C. (300° F.) or from about −18° C. (0° F.) to about 93.3° C. (200° F.). Desirably, the heated air temperature does not exceed 400° F.

Heated air line 284 fluidly connects dryer air heater 280 with dryer 260. Drying zone III may further comprise a heated air distributor 286 configured to divide heated air line 284 into a plurality of heated air dryer inlet lines. For example, in the embodiment of FIG. 5, distributor 286 divides the flow of air from heated air line 284 into three heated air dryer inlet lines 284A-284C. Air passing through dryer 260 may comprise entrained feed material. Accordingly, drying zone III can comprise one or more dryer cyclones 265 configured to separate solids from the air exiting dryer 260. In the embodiment of FIG. 5, air exiting dryer 260 via dryer vent lines 286A-286C is combined via air manifold 287 into dryer vent line 281 which is fed into dryer cyclone 265. It is to be noted that, although three air inlet and air outlet (vent) lines are shown in the embodiment of FIG. 5, any number of air inlet lines and outlet lines may be utilized. Additionally, the number of air inlet lines to dryer 260 need not be equal to the number of air outlet or vent lines.

Dryer cyclone 265 is configured to remove solids from the vent gas exiting dryer 260. Air and any fines entrained therein exit dryer cyclone 265 via dryer cyclone fines outlet line 266, while solids exit dryer cyclone 265 via dryer cyclone solids outlet line 267. Line 267 may be fluidly connected with reformer feed hopper inlet line 276. Dryer cyclone fines outlet line 266 may be configured to introduce air and entrained fines into dryer baghouse 240 along with fines introduced thereto from grinder discharge cyclone 220, grinder discharge cyclone outlet line 222, grinder discharge blower 230 and/or grinder discharge blower outlet line 231. In embodiments, dryer cyclone 265 is configured to provide solids having a particle size of greater than 3⁄32" (2.5 mm) or greater than 3⁄16" (4.8 mm) into dryer cyclone solids outlet line 267. In embodiments, dryer cyclone 265 is configured to separate solids having a particle size of less than 3⁄16" into dryer cyclone fines outlet line 266. In embodiments, dryer cyclone 265 has an efficiency of at least 85, 90, 92, 95, 96, 97, or 98 percent.

One or more dryer baghouses 240 are configured to remove solids from the air introduced thereto. One or more dryer baghouse solids outlet lines 243 are configured to introduce solids separated within dryer baghouse 240 into reformer feed hopper cyclone inlet line 276 of reformer feed hopper zone IV, further discussed hereinbelow. In embodiments, dryer baghouse 240 is configured to provide solids having a particle size of greater than 20, 15, 10 or 5 μm into dryer baghouse solids outlet line 243. In embodiments, dryer baghouse 240 is configured to separate solids having a particle size of less than 10 μm into dryer baghouse fines outlet line 244.

One or more dryer baghouse fines outlet lines 244 are configured to introduce gas from dryer baghouse 240 into dryer stack 246, optionally via dryer exhaust fan 241 and line 247. A line 251 may introduce air into an accumulator 245 prior to introduction into dryer baghouse(s) 240.

Feed handling and/or drying apparatus 200A can further comprise a reformer feed hopper zone IV. The reformer feed hopper zone IV comprises at least one reformer feed hopper and a feeder configured for feeding feed material into mixing apparatus 300. In the embodiment of FIG. 5, reformer feed hopper zone IV comprises reformer feed hopper 295 and mixing vessel rotary feeder 297. Reformer feed hopper zone IV can further comprise a surge hopper 270, a reformer feed hopper blower 275 and a reformer feed hopper cyclone 290, as indicated in the embodiment of FIG. 5. One or more dried feed lines 294 are configured to introduce dried feed material from one or more dryers 260 of dryer zone III into reformer feed hopper zone IV. The feed material may be introduced into a surge hopper 270, configured for storage of surplus dried feed material and supply therefrom to reformer feed hopper 295. A reformer feed hopper blower 275 may be incorporated into zone IV for pushing dried feed material and/or separated solids introduced into reformer feed hopper cyclone inlet line 276 from dryer(s) 260 and/or surge hopper (s) 270 via line(s) 271, from dryer cyclone(s) 265 via dryer cyclone solids outlet line(s) 267, from dryer baghouse(s) 240 via dryer baghouse solids outlet line(s) 243 into reformer feed hopper cyclone(s) 290. In alternative embodiments, the material in reformer feed hopper inlet line(s) 276 is introduced directly into reformer feed hopper 295. Reformer feed hopper cyclone 290 is configured to separate fines from material introduced therein. In embodiments, a reformer feed hopper cyclone outlet line 292 is configured to introduce fines separated within reformer feed hopper cyclone 290 into dryer baghouse 240, optionally via grinder discharge blower outlet line 231 as indicated in the embodiment of FIG. 5. In embodiments, reformer feed hopper cyclone 290 is configured to provide solids having an average particle size in the range of from about 3.9E-5 inch (0.0001 cm) to about 1 inch (2.54 cm), from about 0.01 inch (0.0254 cm) to about 0.5 inch (1.27 cm) or from about 0.09 inch (0.24 cm) to about 0.2 inch (0.51 cm) into reformer feed hopper 295. In embodiments, the feed material in reformer feed hopper 295 is of a size allowing it to pass through a 4.8 millimeter (3/16 inch) screen. In embodiments, reformer feed hopper cyclone 290 is configured to separate solids having a particle size of less than 3/16" (0.48 cm) into reformer feed hopper cyclone fines outlet line 292. Feed material is introduced into reformer feed hopper 295 via reformer feed hopper inlet line 276 and optionally reformer feed hopper cyclone 290. In embodiments, reformer feed hopper 295 is a cylindrical vessel having a conical bottom. In embodiments, reformer feed hopper cyclone 295 provides an efficiency of at least 80, 85, 90, 92, 95, 96, 97 or 98 percent.

Mixing vessel rotary feeder 297 is configured to introduce feed material from reformer feed hopper 295 into mixing apparatus 300. As needed, feed material is fed from reformer feed hopper 295 and rotary feeder 297 into mixing apparatus 300. Rotary feeder 297 may be substantially as described in U.S. Pat. No. 7,375,142. Feed material exits reformer feed hopper 295 via feed hopper outlet line 296, which fluidly connects reformer feed hopper 295 with mixing vessel rotary feeder 297.

In embodiments, one or more purge lines 291 is configured to introduce purge gas (e.g. flue gas or plant air) for purge into and push feed material through reformer feed hopper 295. In embodiments, the purge gas is flue gas comprising about 80% nitrogen and about 20% carbon dioxide, helping to insure that the reformation process in reformer 400 will be carried out anaerobically. Reformer feed hopper 295 may also include a vent for venting flue gas. From reformer feed hopper 295, feedstock settles into feed hopper outlet line(s) 296, which extends from the bottom of reformer feed hopper 295. The feedstock is metered by rotary valve 297 into feedstock inlet line 250, along which it is entrained with steam under pressure entering from superheated steam line 550 of mixing apparatus 300. To keep feedstock flowing into the stream of steam, and in order to counter steam back pressure in line 250, a supply of gas is moved through rotary feeder purge gas inlet line 288 via a compressor to an inlet just below valve 297. To prevent the pressure in feedstock inlet line 250 from blowing feedstock back into rotary valve 297, some of the gas is also split off from rotary feeder purge gas inlet line 288 and fed to an inlet of mixing vessel rotary feeder 297. Rotary feeder 297 includes a central rotor having a plurality of vanes which divide the interior of valve 297 into separate compartments. Opposite the inlet on rotary valve 297, is an outlet pressure vent line 289. As the rotor of valve 297 rotates, the compartment formed by the vanes at the top fill with feedstock. That filled compartment is then rotated until it opens to the inlet, where it is pressurized with incoming gas. As the rotor rotates further, the feedstock filled and pressurized chamber opens into reformer feedstock inlet line 250. Since the pressure in the rotor chamber is equalized with the pressure in line 250, the feedstock falls down into feedstock inlet line 250. As the valve rotor continues on its journey, it is eventually vented through outlet pressure vent line 289, such that when the chamber again reaches feed hopper outlet line 296, it is depressurized and will not vent back up into feed hopper outlet line 296. After feedstock has moved through rotary feeder valve 297 and into feedstock line 250, it feeds by gravity into a mixing chamber or position along mixing apparatus feedstock inlet line 250 where the feedstock is mixed with superheated steam (e.g. steam having a temperature of about 510° C. (950° F.)) from superheated steam line 550.

II. Method of Producing Synthesis Gas Conversion Product. Also disclosed herein is a method of producing synthesis gas conversion product. In embodiments, the conversion product comprises primarily liquid Fischer-Tropsch hydrocarbons. In embodiments, the conversion product comprises primarily alcohols and/or other oxidized compounds.

Figure 6:
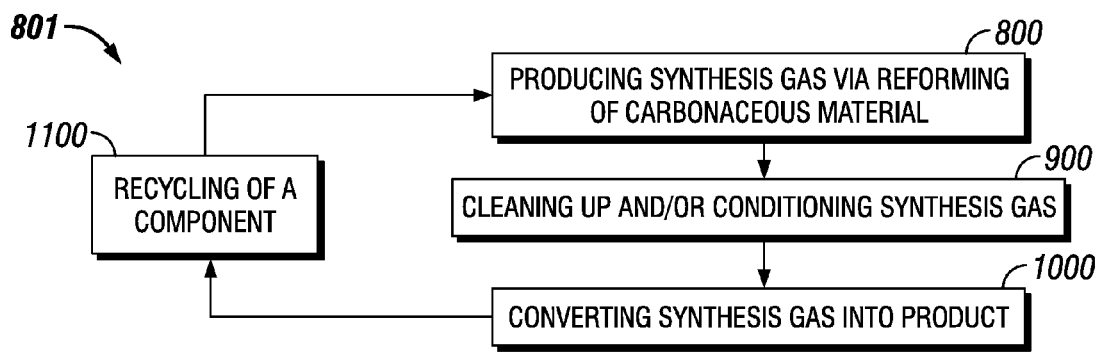
FIG. 6 is a flow diagram of a method of producing synthesis gas conversion product(s) according to an embodiment of this disclosure.

The basic steps in the method of producing synthesis gas conversion product according to this disclosure are depicted in the flow diagram of FIG. 6. As indicated in FIG. 6, a method of producing synthesis gas conversion product 801 comprises producing synthesis gas via reforming of carbonaceous material at 800, cleaning up and/or conditioning the synthesis gas at 900, converting the synthesis gas into product at 1000 and recycling 1100 at least one component from converting at 1000 for reuse in the producing of synthesis gas at 800.

Figure 7:
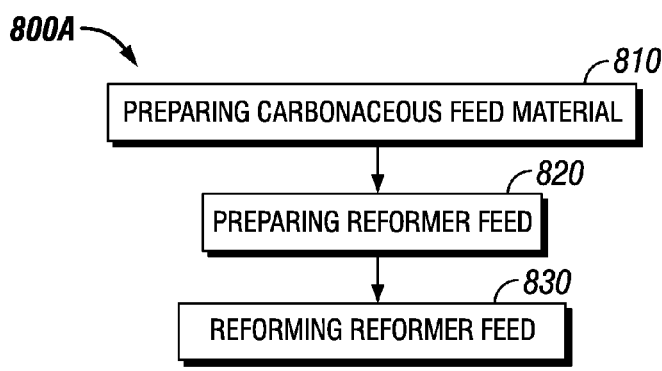
FIG. 7 is a flow diagram of a method of producing synthesis gas according to an embodiment of this disclosure.

Producing Synthesis Gas 800. The method of producing synthesis gas conversion products according to this disclosure comprises producing synthesis gas at 800. FIG. 7 is a flow diagram depicting a method 800A of producing synthesis gas according to an embodiment of this disclosure.

Method 800A comprises preparing carbonaceous feedstock at 810, preparing reformer feed at 820 and reforming the reformer feed at 830. Preparing carbonaceous feed material 810 comprises comminuting and/or drying a suitable carbonaceous feed material. In embodiments, the source of the carbonaceous feedstock comprises biomass. In embodiments, the carbonaceous feedstock comprises at least one component that is or that is derived from lignite, coal, red cedar, southern pine, hardwoods such as oak, cedar, maple and ash, bagasse, rice hulls, rice straw, weeds such as kennaf, sewer sludge, motor oil, oil shale, creosote, pyrolysis oil such as from tire pyrolysis plants, used railroad ties, dried distiller grains, corn stalks and cobs, animal excrement, straw, and combinations thereof.

Preparing Carbonaceous Feedstock 810. In embodiments, preparing the carbonaceous feedstock 810 comprises sizing (comminuting) at least one carbonaceous feedstock such that it is of a desirable size for effective reforming. In embodiments, preparing the carbonaceous feedstock comprises reducing the average particle size of the feedstock to less than about $5/8^{th}$ inch (15.9 mm), ½ inch (12.7 mm), or less than about $3/16^{th}$ of an inch (4.8 mm). The carbonaceous feedstock may be sized by any methods known in the art. In embodiments, a carbonaceous material is sized by introducing it into one or more grinders 210, as discussed above with reference to FIG. 5.

In embodiments, preparing the carbonaceous feed material comprises drying the carbonaceous feedstock to a moisture content in the range of from about 4 weight percent to about 20 weight percent, from about 5 weight percent to about 20 weight percent, from about 10 weight percent to about 20 weight percent or from about 5 weight percent to about 18 weight percent. In embodiments, preparing the carbonaceous feedstock comprises drying the carbonaceous feedstock to a moisture content of less than about 25, 20, 15, 10 or 9 weight percent. The carbonaceous feedstock may be dried by any methods known in the art. In embodiments, a carbonaceous feedstock is dried by introducing it into one or more dryers 260, as discussed above with reference to FIG. 5. In embodiments, ground carbonaceous material exiting grinder 210 is introduced into a grinder discharge cyclone 220. Within grinder discharge cyclone 220, a stream of larger sized particles is separated via grinder discharge cyclone outlet line 225 from a stream of smaller sized particles in grinder discharge fines outlet line 222. A grinder discharge blower 230 may introduce the smaller particles separated in grinder discharge cyclone 220 into one or more dryer baghouse(s) 240. The larger particles exiting grinder discharge cyclone 220 via grinder discharge cyclone outlet line 225 are introduced into dryer 260.

In embodiments, air supplied via air supply fan 261 and line 262 is combined with flue gas in line 570 and introduced into dryer air heater 280. The flue gas utilized here may be produced during reforming of the carbonaceous material discussed below. Heat transfer with steam introduced into the dryer air heater via steam inlet line 560A/560D produces heated air in heated air line 284 and condensate in condensate outlet line 282. As discussed hereinabove, the steam utilized in dryer air heater 280 may be produced via heat transfer with the hot reformer process gas effluent and/or the 'warm' flue gas effluent, as discussed further hereinbelow.

Heated air in heated air line 284 may be divided by a heated air distributor or divider 286 into a plurality of heated air inlet lines 284A-284C. Within dryer 260, the comminuted carbonaceous material is dried to a desired moisture content, as mentioned hereinabove. Dryer effluent comprising air and fines is introduced via dryer vent line 281 into dryer cyclone 265. Dried carbonaceous material exits dryer 260 via one or more dried feed lines 294 and surge hopper 270. Air from reformer feed hopper blower 275 may push comminuted and dried feed material from dryer 260 and surge hopper 270 along reformer feed hopper inlet line 276 into reformer feed hopper cyclone 290. Solids removed from dryer cyclone 265 and dryer baghouse 240 may be introduced into reformer feed hopper inlet line 276, as indicated in FIG. 5.

Gas exiting dryer cyclone 265 may be combined in grinder discharge blower outlet line 231 via dryer cyclone fines outlet line 266 with gas exiting grinder discharge blower 220 and gas exiting reformer feed hopper cyclone 290 via line 292 and introduced into dryer baghouse 240. Gases exiting dryer baghouse via dryer baghouse fines outlet line 244 may pass via dryer exhaust fan 241 and line 247 to dryer stack 246.

Dried carbonaceous materials exit reformer feed hopper cyclone 290 and enter reformer feed hopper 295. Carbonaceous material from reformer feed hopper 295 is introduced via mixing vessel rotary feeder 297 and feedstock line 250 into one or more mixing vessels of mixing apparatus 300.

Preparing Reformer Feed 820. As discussed above, producing synthesis gas via reforming of carbonaceous material 800 further comprises preparing reformer feed 820. A suitable reformer feed may be formed via combination of superheated steam and comminuted and dried carbonaceous material via any methods known in the art. In embodiments, spent catalyst comprising spent catalyst and associated synthesis gas conversion product is combined with the carbonaceous material prior to or along with combination with superheated steam. In embodiments, preparing reformer feed comprises introducing the comminuted and dried carbonaceous feed material and superheated steam into one or more mixing vessels as described hereinabove.

With reference to FIG. 2, preparing reformer feed material can comprise introducing comminuted and dried feed material via lines 250, 250A and 250B into mixing apparatus 300A. Spent catalyst/conversion product may be combined with the carbonaceous material via line 755. In alternative embodiments, spent catalyst/conversion product is introduced directly into the mixing vessel(s). Superheated steam from steam superheater 501B is introduced via superheated steam lines 550, 550A and 550B into mixers 310A and 310B, respectively.

With reference to FIG. 3, preparing reformer feed can comprise introducing comminuted and dried feed material via feedstock inlet line 250 into mixing apparatus 300B. Superheated steam from steam superheater 501B' is introduced via superheated steam line 550 into mixer 310C.

As mentioned hereinabove, within the mixing apparatus, superheated steam and carbonaceous material are combined to provide a reformer feed mixture comprising from about 0.14 kilograms (0.3 pounds) to about 0.0.32 kilograms (0.7 pounds), from about 0.14 kg (0.3 pounds) to about 0.23 kg (0.5 pounds) or from about 0.14 kg (0.3 pounds) to about 0.18 kg (0.4 pounds) of steam is added per pound of 'dry' feedstock comprising from about 4% to about 20% moisture by weight, from about 9% to about 18% moisture or from about 10% to about 20% moisture, to provide the reformer feed mixture that is introduced into the coiled tubes of the reformer. In embodiments, the reformer feed comprises from about 0.01 wt % to about 20 wt %, from about 0.05 wt % to about 10 wt %, or from about 1 wt % to about 5 wt % weight percent spent catalyst/product (e.g. cat/wax). The reformer feed may have a temperature in the range of from about 150° F. (66° C.) to about 1000° F. (538° C.), from about 200° F. (93° C.) to about 750° F. (399° C.), or from about 300° F. (149° C.) to about 400° F. (204° C.). In embodiments, the reformer feed has a pressure of at least or about in the range of from about 34.5 kPa (5 psig) to about 275 kPa (40 psig).

The superheated steam utilized in the reformer feed mixers may be produced by heat exchange with the reformer flue gas effluent and/or the reformer process gas effluent. With reference to FIG. 2, BFW may be introduced via BFW inlet line(s) 580 into reformer effluent and reformer flue gas steam generator 501A. Within reformer effluent and reformer flue gas steam generator 501A, heat transfer between the hot gas (warm reformer flue gas passing through steam superheater 501B and 'hot' reformer process gas effluent) and the BFW may produce steam (in steam outlet line 560) having a temperature in the range of from about 300° F. (148.9° C.) to about 500° F. (260° C.), from about 350° F. (176.7° C.) to about 500° F. (260° C.) or from about 350° F. (176.7° C.) to about 500° F. (260° C.) and a pressure in the range of from about 200 psig (1379 kPa) to about 300 psig (2068.4 kPa), from about 250 psig (1723.7 kPa) to about 300 psig (2068.4 kPa), or from about 275 psig (1896.1 kPa) to about 300 psig (2068.4 kPa). Steam exiting reformer effluent and reformer flue gas steam generator 501A via steam generator steam outlet line 560 may be divided, with a portion entering steam superheater 501B via line 560B and another portion exported via line 560A. Within steam superheater 501B, heat transfer between 'hot' reformer flue gas and steam produces superheated steam having a temperature in the range of from about 400° F. (204.4° C.) to about 1000° F. (537.8° C.), from about 600° F. (315.6° C.) to about 950° F. (510° C.) or from about 400° F. (204.4° C.) to about 900° F. (482.2° C.) and/or a pressure in the range of from about 150 psig (1034.2 kPa) to about 400 psig (2757.9 kPa), from about 200 psig (1379 kPa) to about 375 psig (2585.5 kPa) or from about 250 psig (1723.7 kPa) to about 350 psig (2413.2 kPa). The superheated steam exiting steam superheater 501B is introduced into reformer feed mixing vessels 310A/310B via lines 550 and 550A/550B.

With reference to FIG. 3, BFW may be introduced via BFW inlet line 580 into reformer effluent steam generator 501A'. Within reformer effluent steam generator 501A', heat transfer between the hot process gas effluent and the BFW may produce steam. Steam exiting reformer effluent steam generator 501A' via line 580A may be introduced into flue gas steam generator 501A". Within flue gas steam generator 501A", heat transfer between 'warm' reformer flue gas and steam produces saturated steam (exiting via steam generator steam outlet line 560) having a temperature in the range of from about 300° F. (148.9° C.) to about 500° F. (260° C.), from about 350° F. (176.7° C.) to about 500° F. (260° C.) or from about 350° F. (176.7° C.) to about 500° F. (260° C.) and a pressure in the range of from about 200 psig (1379 kPa) to about 300 psig (2068.4 kPa), from about 250 psig (1723.7 kPa) to about 300 psig (2068.4 kPa), or from about 275 psig (1896.1 kPa) to about 300 psig (2068.4 kPa).

Reformer flue gas exiting the reformer via reformer flue gas outlet line 470 passes through steam superheater 501B', wherein the temperature of the 'hot' flue gas is reduced to a temperature in the range of from about 530° F. (276.7° C.) to about 1500° F. (815.6° C.), from about 530° F. (276.7° C.) to about 1200° F. (648.9° C.) or about 530° F. (276.7° C.) and/or a pressure in the range of from about −20 inches $H_2O$ to 0 inch $H_2O$; from about −15 inch $H_2O$ to about −5 inch $H_2O$; or from about −10 inches $H_2O$ to about −5 inches $H_2O$ and superheated steam are produced. The superheated steam may have a temperature in the range of from about 400° F. (204.4° C.) to about 1000° F. (537.8° C.), from about 600° F. (315.6° C.) to about 950° F. (510° C.) or from about 400° F. (204.4° C.) to about 900° F. (482.2° C.) and/or a pressure in the range of from about 150 psig (1034.2 kPa) to about 400 psig (2757.9 kPa), from about 200 psig (1379 kPa) to about 375 psig (2585.5 kPa) or from about 250 psig (1723.7 kPa) to about 350 psig (2413.2 kPa). The superheated steam exiting steam superheater 501B' is introduced into reformer feed mixing vessel 310C via line 550.

Reforming Reformer Feed 830. As discussed above, producing synthesis gas via reforming of carbonaceous material 800 further comprises reforming the reformer feed at 830. In embodiments, reforming the reformer feed 830 comprises converting the reformer feed into synthesis gas via introduction into a reformer as described above. Reforming of the synthesis gas will now be described with reference to FIGS. 2 and 3. Reformer feed is introduced into the reformer via one or more reformer feed inlet lines 350. In embodiments, a distributor 412 distributes the reformer feed evenly among a plurality of coiled tubes 410. Within the coiled tubes, reforming of the carbonaceous feedstock produces synthesis gas. In embodiments, the temperature of the reformer (e.g. reformer effluent) is maintained in the range of up to or about 926° C. (1700° F.), 982° C. (1800° F.), 1038° C. (1900° F.), 1093° C. (2000° F.), 1149° C. (2100° F.). In embodiments, the pressure of the reformer is maintained in the range of from about 0 psig (0 kPa) to about 100 psig (689.5 kPa), from about 2 psig (13.8 kPa) to about 60 psig (413.7 kPa) or from about 5 psig (34.5 kPa) to about 50 psig (344.7 kPa). In embodiments, the reformer pressure is maintained at a pressure of equal to or greater than about 2 psig (13.8 kPa), about 5 psig (34.5 kPa), or about 50 psig (344.7 kPa).

The heat needed to maintain the desired reformer temperature is provided to the endothermic reforming process by the combustion of fuel in one or more burners 404. Air for the combustion may be heated in air preheater 413 prior to burning with the fuel in burners 404. The fuel combusted in the burner(s) 404 may be selected from tailgas (e.g. Fischer-Tropsch tailgas), synthesis gas, methane (e.g. natural gas), and combinations thereof Desirably, at least a portion of the fuel combusted in at least one of the burner(s) 404 comprises tailgas recycled from the step of converting the synthesis gas into product 1000. At least one of the burner(s) 404 may be specially designed for the combustion of tailgas or for the combustion of tailgas in combination with another gas, for example in combination with a as selected from synthesis gas and methane (e.g. natural gas). In embodiments, recycle tailgas in line(s) 770 is introduced into one or more burner(s) 404 by introduction into one or more of the fuel lines 406 or via another fuel inlet line(s).

Cleaning Up and/or Conditioning Synthesis Gas 900. The method of producing synthesis gas conversion products according to this disclosure further comprises cleaning up and/or conditioning the synthesis gas at 900. Cleaning up and/or conditioning the synthesis gas comprises removing one or more components from the synthesis gas. Cleaning up and/or conditioning the synthesis gas can comprise removing one or more components selected from the group consisting of ash, tar, aromatics, carbon dioxide, hydrogen sulfide, carbon monoxide and hydrogen from the synthesis gas. In embodiments, the synthesis gas is introduced into one or more cyclones and/or baghouses for the removal of ash. The ash may be reduced to a level of less than 10 weight percent, less than about 1.0 weight percent or less than about 0.1 weight percent. In embodiments, tar is removed from the synthesis gas. In embodiments, the synthesis gas is introduced into a venturi scrubber that serves to remove water-soluble hydrocarbons, tar, ash fines that escaped the ash removal apparatus and/or benzene from the synthesis gas.

In embodiments, aromatics are removed from the synthesis gas. In embodiments, ash and/or tar-reduced synthesis gas is introduced into a TEG unit whereby solvent extraction reduces the level of tars and/or aromatics therein.

In embodiments, conditioning comprises removing carbon dioxide from the synthesis gas. In embodiments, an acid gas removal unit is utilized to remove carbon dioxide and hydrogen sulfide from the synthesis gas. The AGRU may be downstream of a TEG unit.

In embodiments, conditioning comprises subjecting the synthesis gas to water gas shift by reaction of carbon monoxide in the synthesis gas with water to produce carbon dioxide and additional hydrogen, thus reducing the carbon monoxide content of the synthesis gas. In embodiments, water gas shift provides a synthesis gas having a mole ratio of hydrogen to carbon monoxide in the range of from about 0.5:1 to about 1.1:1, from about 0.7:1 to about 1.1:1, or about 1:1.

In embodiments for which the synthesis gas will be used at step 1000 for the production of liquid Fischer-Tropsch hydrocarbons, the cleaned-up and conditioned synthesis gas may have a molar ratio in the range of from about 0.5:1 to about 1.1:1, from about 0.7:1 to about 1.1:1, or about 1:1, a tar content of less than about 200 ppm (e.g. ~95% removal), a carbon dioxide content of less than about 10 weight % (e.g. ~95 percent removal), a sulfur content of less than about 1 ppm, a BTEX content of less than about 50 ppm (e.g. ~95% removal), an ash content of less than about 0.1 weight percent, or a combination thereof.

Converting Synthesis Gas into Product 1000. The method of producing synthesis gas conversion product according to this disclosure further comprises converting the synthesis gas into product at 1000. Desirably, the conversion produces, in addition to valuable primary products, a tailgas suitable for recycle to the step of producing synthesis gas via reforming 800, as further discussed hereinbelow. In embodiments, the tailgas comprises one or more gas selected from carbon dioxide, methane, hydrogen (e.g. unreacted hydrogen) and carbon monoxide (e.g. unreacted carbon monoxide).

Figure 8:
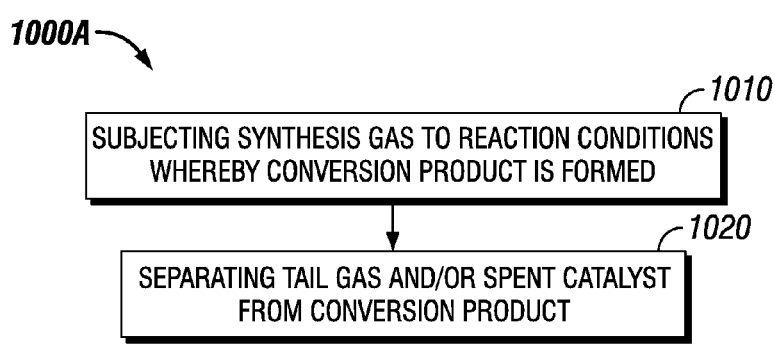
FIG. 8 is a flow diagram of a method for converting synthesis gas to product according to an embodiment of this disclosure.

The cleaned and/or conditioned synthesis gas is converted into valuable products at 1000. This conversion may be referred to herein as Fischer-Tropsch conversion. FIG. 8 is a flow diagram of a method 1000A for converting synthesis gas to product, according to an embodiment of this disclosure. Method 1000A comprises subjecting the synthesis gas to reaction conditions whereby conversion products are formed 1010 and separating tailgas and/or spent catalyst/product from the conversion product(s) 1020.

Converting synthesis gas into product comprises subjecting the synthesis gas to reaction conditions whereby conversion products are formed. In embodiments, the synthesis gas is converted into products consisting primarily of alcohols and/or other oxidized compounds. Suitable reaction conditions including temperatures, pressures and catalysts for such conversion are known in the art.

In embodiments, the synthesis gas is converted into products consisting primarily of liquid hydrocarbons. In embodiments, the synthesis gas is converted into products consisting primarily of $C^{5+}$ hydrocarbons. In such embodiments, the synthesis gas may be compressed, as needed, and introduced into one or more Fischer-Tropsch reactors configured for the production of liquid hydrocarbons. In such embodiments, subjecting the synthesis gas to reaction conditions whereby conversion products are formed can comprise contacting the synthesis gas with an FT catalyst that promotes the FT synthesis reactions at suitable temperatures and pressures as known in the art.

In embodiments, the catalyst comprises at least one catalytically active metal or oxide thereof. In embodiments, the catalyst further comprises a catalyst support. In embodiments, the catalyst further comprises at least one promoter. The catalytically active metal may be selected from the group consisting of Co, Fe, Ni, Ru, Re, Os, and combinations of two or more thereof. The support material may comprise alumina, zirconia, silica, aluminum fluoride, fluorided alumina, bentonite, ceria, zinc oxide, silica-alumina, silicon carbide, a molecular sieve, or a combination of two or more thereof. The support material may comprise a refractory oxide. The promoter may be selected from Group IA, IIA, IIIB or IVB metals and oxides thereof, lanthanide metals and metal oxides, and actinide metals and metal oxides. In embodiments, the promoter is selected from the group consisting of Li, B, Na, K, Rb, Cs, Mg, Ca, Sr, Ba, Sc, Y, La, Ac, Ti, Zr, La, Ac, Ce and Th, oxides thereof, and mixtures of two or more thereof. Suitable catalysts may be as disclosed in U.S. Pat. Nos. 4,585,798; 5,036,032; 5,733,839; 6,075,062; 6,136,868; 6,262,131; 6,353,035; 6,368,997; 6,476,085; 6,451,864; 6,490,880; 6,648,662; 6,537,945; 6,558,634; and U.S. Patent App. No. 2003/0105171; these patents and patent publications being incorporated herein by reference for their disclosures of Fischer-Tropsch catalysts and methods for preparing such catalysts.

The FT catalyst can be any suitable catalyst known in the art. In embodiments, the FT catalyst is an iron-based catalyst formed as described in or having the composition of an FT catalyst described in U.S. Pat. No. 5,508,118 and/or U.S. patent application Ser. Nos. 12/189,424; 12/198,459; 12/207,859; 12/474,552; and/or 12/790,101, the disclosures of each of which are hereby incorporated herein in their entirety for all purposes not contrary to this disclosure.

In embodiments, the FT catalyst is an iron-based catalyst comprising iron, copper and potassium. The catalyst may have a weight ratio of 100Fe:1Cu:1K (wt %:wt %:wt %), wherein the iron in the catalyst comprises a maghemite:hematite weight ratio in the range of about 1%:99% to about 70%:30%. The iron catalyst can comprise a maghemite to hematite ratio of about 10%:90%. The catalyst can have a particle size distribution in the range of 10 μm-100 μm. The catalyst can exhibit a BET surface area in the range of from about 45 $m^2/g$ to about 150 $m^2/g$ or from about 45 $m^2/g$ to about 65 $m^2/g$. The catalyst can have a mean pore diameter in the range of from about 45 Å to about 120 Å or from about 75 Å to about 120 Å. The catalyst can have a mean pore volume in the range of from about 0.2 cc/g to about 0.6 cc/g or from about 0.20 cc/g to about 0.24 cc/g. The catalyst can have a mean crystallite size in the range of from about 15 nm to about 40 nm or from about 25 nm to about 29 nm.

Depending on the preselected alpha, i.e., the polymerization probability desired, a precipitated iron catalyst may have a weight ratio of potassium (e.g., as carbonate) to iron in the range of from about 0.005 and about 0.015, in the range of from 0.0075 to 0.0125, or about 0.010. Larger amounts of alkali metal promoter (e.g., potassium) may cause the product distribution to shift toward the longer-chain molecules, while small amounts of alkali metal may result in a predominantly gaseous hydrocarbon product.

The weight ratio of copper to iron in the iron Fischer-Tropsch catalyst may be in the range of from about 0.005 and 0.050, in the range of from about 0.0075 and 0.0125, or about 0.010. Copper may serve as an induction promoter. In preferred embodiments, the weight ratio of Cu:Fe is about 1:100.

The catalyst may be an iron Fischer-Tropsch catalyst comprising structural promoter. The structural promoter may significantly reduce the breakdown of the catalyst in a SBCR (slurry bubble column reactor). The structural promoter may comprise silica, and may enhance the structural integrity during activation and operation of the catalyst. In embodiments, the catalyst comprises a mass ratio of $SiO_2$:Fe of less than about 1:100 when the structural promoter comprises silica and less than about 8:100 when the structural promoter comprises silica sol.

In embodiments, the at least one structural promoter is selected from oxides of metals and metalloids and combinations thereof The structural promoter may be referred to as a binder, a support material, or a structural support.

Depending on the level of structural promoter comprising silicate and the preselected alpha, i.e. the polymerization probability desired, the weight ratio of K:Fe may be from about 0.5:100 to about 6.5:100, from about 0.5:100 to about 2:100, or about 1:100.

In embodiments wherein the structural promoter comprises silica sol, the weight ratio of iron to potassium is in the range of from about 100:1 to about 100:5. In embodiments, the weight ratio of iron to potassium is in the range of from about 100:2 to about 100:6. In embodiments, the weight ratio of iron to potassium is in the range of from about 100:3 to about 100:5. In embodiments, the weight ratio of iron to potassium is in the range of from about 100:4 to about 100:5. In some preferred embodiments, the weight ratio of iron to potassium is in the range of from about 100:2 to about 100:4. In embodiments, the weight ratio of iron to potassium about 100:3. In embodiments, the weight ratio of iron to potassium is about 100:5.

In embodiments wherein the structural promoter comprises silica sol, the weight ratio of iron to copper may be in the range of from about 100:1 to about 100:7. In some embodiments, the weight ratio of iron to copper is in the range of from about 100:1 to about 100:5. More preferably, the weight ratio of iron to copper is in the range of from about 100:2 to about 100:6. Still more preferably, the weight ratio of iron to copper is in the range of from about 100:3 to about 100:5. In some preferred embodiments, the weight ratio of iron to copper is in the range of from about 100:2 to about 100:4. In other specific embodiments, the weight ratio of iron to copper is about 100:5. In yet other specific embodiments, the weight ratio of iron to copper is about 100:3.

Broadly, in embodiments, wherein the structural promoter is silica sol, the iron to $SiO_2$ weight ratio may be in the range of from about 100:1 to about 100:8; alternatively, in the range of from 100:1 to 100:7. In embodiments, wherein the structural promoter is silica, the iron to $SiO_2$ weight ratio may be in the range of from about 100:2 to about 100:6. In embodiments, the weight ratio of iron to silica is in the range of from about 100:3 to about 100:5. In embodiments, wherein the structural promoter is silica, the iron to $SiO_2$ weight ratio is about 100:5. In embodiments, wherein the structural promoter is silica, the iron to $SiO_2$ weight ratio may be in the range of from about 100:3 to about 100:7; alternatively, in the range of from about 100:4 to about 100:6. In embodiments, the catalyst comprises an Fe:Cu:K:$SiO_2$ mass ratio of about 100:4:3:5.

In embodiments, the FT catalyst is a cobalt-based catalyst. In embodiments, the catalyst comprises cobalt, and optionally a co-catalyst and/or promoter, supported on a support wherein the cobalt loading is at least or about 5, 10, 15, 20, 25, 28, 30, 32, 35, or 40 percent by weight. In embodiments, the cobalt loading is in the range of from about 5 to about 50% by weight, from about 10 to about 50% by weight, from about 15 to about 50% by weight, from about 20 to about 50% by weight, from about 25 to about 50% by weight, from about 28 to about 50% by weight, from about 30 to about 50% by weight, or from about 32 to about 50% by weight. The metal dispersion for the catalytically active metal (e.g., Co, and optionally co-catalyst and/or promoter) of the catalyst may be in the range of from about 1 to about 30%, from about 2 to about 20%, or from about 3 to about 20%. In embodiments, the co-catalyst is selected from the group consisting of Fe, Ni, Ru, Re, Os, oxides thereof, and mixtures of two or more thereof. In embodiments, the catalyst comprises at least one promoter selected from the group consisting of Group IA, IIA, IIIB or IVB metals, oxides thereof, lanthanide metals and oxides thereof, and actinide metals and oxides thereof. In embodiments, the promoter is selected from the group consisting of Li, B, Na, K, Rb, Cs, Mg, Ca, Sr, Ba, Sc, Y, La, Ac, Ti, Zr, La, Ac, Ce, Th, oxides thereof, and mixtures of two or more thereof. The co-catalyst may be employed at a concentration in the range of from about 0 to about 10% by weight based on the total weight of the catalyst (i.e., the weight of catalyst, co-catalyst, promoter and support) or from about 0.1 to about 5% by weight. The promoter may be employed at a concentration of up to about 10% by weight based on the total weight of the catalyst, and in one embodiment about 0.1 to about 5% by weight.

In embodiments, the catalyst comprises cobalt supported by alumina; the loading of cobalt being at least about 25% by weight, at least about 28% by weight, at least about 30% by weight, or at least about 32% by weight; and the cobalt dispersion is at least about 3%, at least about 5%, or at least about 7%.

In embodiments, the catalyst used in the disclosed method is a FT catalyst as described in and/or formed via the multiple impregnation step method described in U.S. Pat. No. 7,084,180, the disclosure of which is hereby incorporated herein in its entirety for all purposes not contrary to this disclosure. The catalyst can comprises at least one catalytic metal (i.e., Co, Fe) at a loading level of about 20% by weight or more, about 25% by weight or more, about 28% by weight or more, about 30% by weight or more, about 32% by weight or more, about 35% by weight or more, about 37% by weight or more, or about 40% by weight or more.

In embodiments, the FT catalyst utilized is an iron-based catalyst and subjecting the synthesis gas to reaction conditions whereby liquid hydrocarbons are produced comprises contacting the synthesis gas with catalyst at a temperature in the range of from about 200° C. (392° F.) to about 300° C. (572° F.), from about 220° C. (428° F.) to about 275° C. (527° F.) or from about 240° C. (464° F.) to about 260° C. (500° F.). In embodiments, the temperature of the FT synthesis is a temperature of greater than or equal to about 200° C. (392° F.), 220° C. (428° F.) or 250° C. (482° F.). In embodiments, the FT synthesis is carried out at a pressure in the range of from about 100 psig (689.5 kPa) to about 1000 psig (6894.8 kPa), from about 200 psig (1379 kPa) to about 500 psig (3447.4 kPa) or from about 300 psig (2068.4 kPa) to about 400 psig (2757.9 kPa). In embodiments, the FT synthesis is carried out at a pressure of greater than or equal to about 100 psig (689.5 kPa), about 300 psig (2068.4 kPa), or about 350 psig (2413.2 kPa). In embodiments, the FT synthesis is carried by introducing the synthesis gas into an FT production apparatus 700, as described hereinabove. The FT production apparatus comprises an FT synthesis reactor. In embodiments, the FT synthesis reactor is a slurry bubble column reactor. In embodiments, the residence time in the FT synthesis reactor is in the range of from about 1 s to about 3000 s, from about 10 s to about 500 s or from about 100 s to about 300 s. In embodiments, the FT synthesis is carried out for a residence time of about 100 s, about 200 s, or about 300 s.

Converting synthesis gas into product can further comprise separating tailgas and/or spent catalyst/product from the conversion product at 1020. In embodiments, converting synthesis gas into product further comprises separating tailgas from the primary product(s). For example, a tailgas comprising methane, hydrogen, carbon monoxide and/or carbon dioxide may be separated from the synthesis gas conversion product (e.g. liquid hydrocarbons). In embodiments, converting synthesis gas into product further comprises separating spent catalyst/wax from the liquid hydrocarbons. During FT synthesis of liquid hydrocarbons, spent catalyst and associated wax is routinely removed from the slurry process. Such catalyst can be separated from the primary liquid product via any suitable methods known in the art, for example via centrifugation, filtration, magnetic separation, or a combination thereof Such separated spent catalyst and any product that is separated therewith is referred to herein as spent catalyst/product and may be recycled, as discussed further hereinbelow, in step 1100.

Recycling at least one Component 1100. In embodiments, the disclosed method of producing synthesis gas conversion product according to this disclosure comprises recycling at least one component from converting at 1000 for reuse in producing additional synthesis gas 800.

In embodiments, recycling at least one component 1100 comprises recycling at least a portion of the tailgas produced while converting the synthesis gas to product at 1000. The tailgas produced during conversion of synthesis gas to product can be recycled for use as fuel in the reforming step. In this manner, the 'waste' tailgas can be utilized to benefit within the system. As discussed hereinabove, one or more tailgas recycle lines 770 may fluidly connect the FT synthesis apparatus 700 with one or more burners 404 of reformer 400. As discussed hereinabove, carbon dioxide may be removed from the tailgas prior to recycle for use as fluid. This may be particularly desirable as it enables sequestration of additional carbon dioxide within the biorefinery. All or a portion of the tailgas exiting synthesis gas conversion apparatus 700 via tailgas outlet line 760 can be introduced into a carbon dioxide removal apparatus, described hereinabove, and/or recycled to reformer 400.

In embodiments, recycling at least one component 1100 comprises recycling at least a portion of the separated spent catalyst/product and subjecting it to reforming conditions along with carbonaceous feed material to produce additional synthesis gas from the product (e.g. liquid hydrocarbons) therein. For example, one or more catalyst/product recycle lines 755 may be used to introduce spent catalyst/product into the reformer, for example via carbonaceous feed line 250 and/or mixing apparatus 300. In this manner, additional value can be obtained from the reformable material separated with the spent catalyst, thus improving the overall liquid yields of the biorefinery. Additionally, in this manner, disposal of material is reduced and the spent catalyst (substantially free of associated product) can be separated (e.g. with the ash) for disposal. At least a portion of the spent catalyst/product separated from the primary conversion product(s) at 1020 can thus be recycled through the coiled tubes of the reformer for production of additional synthesis gas therefrom.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A method of producing synthesis gas conversion product, the method comprising:
    reforming a carbonaceous feedstock comprising at least one carbonaceous material to produce a first synthesis gas comprising hydrogen, and carbon monoxide;
    subjecting at least a portion of the first synthesis gas to catalytic conversion whereby at least a portion of the hydrogen and carbon monoxide therein is converted into synthesis gas conversion product;
    separating from the synthesis gas conversion product a spent catalyst product comprising synthesis gas conversion product and catalyst that has been at least partially deactivated, attrited, or both during catalytic conversion; and
    utilizing at least a portion of the spent catalyst product during reforming of additional carbonaceous material.

2. The method of claim 1 wherein the catalytic conversion comprises Fischer-Tropsch conversion of synthesis gas and wherein the synthesis gas conversion product comprises liquid hydrocarbons.

3. The method of claim 2 wherein the catalyst is selected from the group consisting of iron-based Fischer-Tropsch catalysts.

4. The method of claim 2 further comprising separating from the synthesis gas conversion product a wherein the byproduct comprises Fischer-Tropsch tailgas comprising at least one component selected from carbon monoxide, hydrogen, methane and carbon dioxide, and utilizing at least a portion of the Fischer-Tropsch tailgas during reforming of additional carbonaceous material.

5. The method of claim 4 wherein utilizing at least a portion of the Fischer-Tropsch tailgas during reforming of additional carbonaceous material comprises combusting at least a portion of the Fischer-Tropsch tailgas to provide heat for reforming additional carbonaceous material.

6. The method of claim 5 further comprising removing carbon dioxide from the Fischer-Tropsch tailgas.

7. The method of claim 2 wherein the spent catalyst product comprises liquid hydrocarbons and catalyst.

8. The method of claim 7 wherein utilizing at least a portion of the spent catalyst product during reforming of additional carbonaceous material comprises reforming at least a portion of the spent catalyst product with additional carbonaceous material.

9. The method of claim 1 further comprising preparing the carbonaceous feedstock by combining at least one carbonaceous material with superheated steam.

10. The method of claim 9 wherein the carbonaceous feedstock is prepared at a pressure of between about 5 psig (34.5 kPa) to 45 psig (310.3 kPa).

11. The method of claim 9 further comprising providing a desired molar ratio of hydrogen to carbon monoxide in the first synthesis gas by controlling at least one parameter selected from the group consisting of the weight ratio of the at least one carbonaceous material to the superheated steam, the moisture content of the at least one carbonaceous material, the reforming temperature, and the reforming pressure.

12. The method of claim 11 wherein the reforming temperature is in the range of from about 1700° F. (926° C.) to about 2200° F. (1204° C.).

13. The method of claim 11 wherein the catalytic conversion comprises Fischer-Tropsch conversion of synthesis gas, wherein the synthesis gas conversion product comprises liquid hydrocarbons and wherein the desired molar ratio is in the range of from about 0.5:1 to about 2:1.

14. The method of claim 13 wherein the desired molar ratio is about 1:1.

15. The method of claim 1 further comprising reducing the amount of at least one component selected from the group consisting of hydrogen, carbon monoxide, ash, tar, aromatics and carbon dioxide in the first synthesis gas.

16. The method of claim 1 wherein the catalytic conversion comprises conversion of synthesis gas into at least one component selected from the group consisting of alcohols and wherein the catalyst favors the production thereof.

17. The method of claim 1 wherein the carbonaceous feedstock comprises biomass.

18. The method of claim 1 further comprising producing superheated steam utilizing the heat of a flue gas produced during reforming, the heat of the first synthesis gas, or both.

* * * * *

UNITED STATES PATENT AND TRADEMARK OFFICE
CERTIFICATE OF CORRECTION

| | | |
|---|---|---|
| PATENT NO. | : 8,093,306 B2 | Page 1 of 1 |
| APPLICATION NO. | : 12/976739 | |
| DATED | : January 10, 2012 | |
| INVENTOR(S) | : Randy Blevins et al. | |

It is certified that error appears in the above-identified patent and that said Letters Patent is hereby corrected as shown below:

Column 34, line 37, cancel the text beginning "wherein the" and ending "byproduct comprises" in column 34, line 38, as shown below:

4. The method of claim 2 further comprising separating from the synthesis gas conversion product a ~~wherein the byproduct comprises~~ Fischer-Tropsch tailgas comprising at least one component selected from carbon monoxide, hydrogen, methane and carbon dioxide, and utilizing at least a portion of the Fischer-Tropsch tailgas during reforming of additional carbonaceous material.

Signed and Sealed this
Twentieth Day of March, 2012

David J. Kappos
*Director of the United States Patent and Trademark Office*